United States Patent
Zhao et al.

(10) Patent No.: US 11,306,350 B2
(45) Date of Patent: Apr. 19, 2022

(54) PRIMERS, COMPOSITIONS, AND METHODS FOR NUCLEIC ACID SEQUENCE VARIATION DETECTION

(71) Applicant: Maccura Biotechnology Co., Ltd., Chengdu (CN)

(72) Inventors: Yuhang Zhao, Chengdu (CN); Shufang Wang, Chengdu (CN); Zhiqi Ge, Chengdu (CN)

(73) Assignee: Maccura Biotechnology Co., Ltd., Chengdu (CN)

( * ) Notice: Subject to any disclaimer, the term of this patent is extended or adjusted under 35 U.S.C. 154(b) by 31 days.

(21) Appl. No.: 16/384,262

(22) Filed: Apr. 15, 2019

(65) Prior Publication Data
US 2020/0102606 A1 Apr. 2, 2020

(30) Foreign Application Priority Data
Sep. 30, 2018 (CN) .......................... 201811158671.5

(51) Int. Cl.
*C12Q 1/6851* (2018.01)
*C12Q 1/6827* (2018.01)

(52) U.S. Cl.
CPC ......... *C12Q 1/6851* (2013.01); *C12Q 1/6827* (2013.01); *C12Q 2600/156* (2013.01)

(58) Field of Classification Search
CPC ....................... C12Q 1/6858; C12Q 2531/113
See application file for complete search history.

(56) References Cited

U.S. PATENT DOCUMENTS 6,270,967 B1 * 8/2001 Whitcombe ......... C12Q 1/6858
435/6.12

2015/0361475 A1 * 12/2015 Marras ................. C12Q 1/686
435/91.2

FOREIGN PATENT DOCUMENTS

WO WO-2017176852 A1 * 10/2017 ........... C12Q 1/6876

OTHER PUBLICATIONS

Sayers E.W. et al., GenBank, Nucl. Acids Res., vol. 47, pp. D94-D99 (Year: 2018).*
Rickert, A.M. et al., Multiplexed Real-time PCR Using Universal Reporters, Clinical Chem., vol. 50, pp. 1680-1683 (Year: 2004).*

(Continued)

*Primary Examiner* — Teresa E Strzelecka
(74) *Attorney, Agent, or Firm* — Syncoda LLC; Feng Ma

(57) ABSTRACT

Specific, accurate, and cost effective primers for performing digital PCR, compositions and kits containing the primer and methods for using and making the same are useful for detecting nucleic acid mutations. A primer useful as a first forward primer in performing digital PCR to detect a target nucleic acid in a sample, includes: a detection portion located upstream to a target sequence binding portion, and including a second forward primer binding portion having a sequence substantially complementary to a second forward primer, and a probe binding portion downstream to the second forward primer binding portion having a sequence substantially complementary to a probe; the target sequence binding portion includes a mismatch portion having a sequence not complementary to the target nucleic acid, and an amplification determinant portion downstream to the mismatch portion having a sequence complementary to a gene allele or a variant thereof encoded by the target nucleic acid.

20 Claims, 18 Drawing Sheets

Specification includes a Sequence Listing.

(56) References Cited

OTHER PUBLICATIONS

Qiagen QuantiNova Multiplex RT-PCR Handbook, pp. 1-40 (Year: 2017).*
Weiner, M.P. et al., Kits and their unique role in molecular biology: a brief retrospective, Biotechniques, vol. 44, pp. 701-704 (Year: 2008).*
Pekin, D. et al., Quantitative and Sensitive detection of rare mutations using droplet-based microfluidics, Lab on a Chip, vol. 11, pp. 2156-2166 (Year: 2011).*

* cited by examiner

PRIMERS, COMPOSITIONS, AND METHODS FOR NUCLEIC ACID SEQUENCE VARIATION DETECTION

CROSS-REFERENCE TO RELATED APPLICATIONS

The present application claims priority to Chinese Patent Application No. 201811158671.5 filed on Sep. 30, 2018, the disclosure of which is hereby incorporated by reference in its entirely.

SEQUENCE LISTING

This application contains a sequence listing, which is submitted as an ASCII text file in the form of the file named MBE20181041-sequence-listing.txt, created on Apr. 15, 2019 and having 6,890 bytes, the content of which is incorporated herein in its entirety.

BACKGROUND

Polymerase chain reaction (PCR) is a molecular biology technique for enzymatically replicating DNA molecules in vitro. The technique has been commonly applied in many medical and biological research settings to undertake a great variety of tasks, such as gene cloning, phenotypic identification of laboratory animals, transcriptome research, detection of genetic diseases, identification of gene fingerprints, diagnosis of infectious diseases, paternity identification, and so on. Due to its unparalleled replication capability and accuracy, PCR is considered a preferred method for nucleic acid detection by molecular biologists. In the late 1990s, the introduction of real-time quantitative PCR (qPCR) technology and related techniques by Applied Biosystems, Inc. (ABI) further advanced PCR technology into a highly sensitive, specific, and precise nucleic acid sequence analysis technology.

SUMMARY

The present disclosure relates generally to the field of molecular biology, and more specifically to a digital polymerase chain reaction (PCR) primer-pair constructs, compositions thereof, and methods for using the same for the detection of nucleic acid sequence variations. More particularly, the present disclosure relates to a digital PCR primer construct having improved discrimination power in detecting nucleic acid sequence variations among different nucleic acids, compositions comprising said primer, kits containing said primer and the various uses of the same.

In some embodiments, the present disclosure provides a novel digital PCR primer construct, compositions comprising said primers, kits containing said primers, and methods for using the same. Primers, compositions, kits and methods disclosed herein can effectively solve the cross-reaction problem associated with prior art digital PCR approaches that hampers the detection of sequence variation or mutations in target nucleic acid sequences.

In a first aspect, the present disclosure provides a primer-pair construct suitable for use as digital PCR primers for detecting a sequence variation in a target nucleic acid.

Primer pairs in accordance with the present disclosure will generally include a first forward primer (F1) and a reverse primer (R).

The first forward primer (F1) will generally comprise the structural elements of a detection region upstream to a target sequence binding region (in 5'-to-3' order), wherein the upstream detection region and the target sequence binding region can have one or more of the following features:

(1) the target sequence binding region includes an amplification determinant site located at the 3'-end of the region and a mismatch region upstream to the amplification determinant site, wherein the amplification determinant site is complementary to the mutation detection site on a target sequence, and the mismatch region contains one or more bases that are not sequentially complementary to the target sequence;

(2) the upstream detection region comprises a first portion (a) having a sequence identical to a second forward primer (F2), and a second portion (b) having a sequence identical to a probe (P).

In general, the reverse primer is not particularly limited and can be designed by employing any conventional technique known in the art following the principle of nucleic acid base complementarity. In some embodiments, the reverse primer is a conventional primer complementary to a sequence downstream of the mutation detection site on a target sequence.

Preferably, first forward primer (F1) and the second forward primer (F2) can each form a working primer pair with the same reverse primer (R). More preferably, the complementary region between a reverse primer (R) and a target sequence is located around 0-200 bp (or alternatively 0-100 bp, or 0-50 bp) downstream of a complementary region between the forward primer and the target sequence.

It will be understood by those skilled in the art that the designation of forward primer and reverse primer may be interchanged if the sense and antisense chains are switched.

In some other embodiments, the melting temperature ($T_m$) of the first forward primer (F1) is different from that of the second forward primer (F2). In some preferred embodiments, the $T_m$ value of the target sequence binding region of the first forward primer (F1) is higher than that of the second forward primer (F2). In some other preferred embodiments, the $T_m$ value of the target sequence binding region of the first forward primer (F1) is higher than that of the second forward primer (F2) by 5-20° C., and more preferably, by 10-15° C.

The mismatch region of the forward primer (F1) preferably has a length of between 1 to 15 bases (e.g., 1, 2, 3, 4, 5, 6, 7, 8, 9, 10, 11, 12, 13, 14 or 15 bases).

In still some other embodiments of the first forward primer (F1), a distance between the amplification determinant site and the mismatch region can be between 0 to 20 bases.

In some embodiments of the first forward primer (F1), the 3'-end of the amplification determinant site is the 3'-end of the first forward primer. In other words, the amplification determinant site is located at the very 3'-end of the first forward primer (F1), and there are no other bases downstream of the site. In other embodiments of the first forward primer (F1), between 1 to 10 bases downstream of the amplification determinant site is allowed.

In still some embodiments of the first forward primer (F1), a spacer sequence of one or more bases are placed between the first portion (a) and the second portion (b) of the upstream detection region. In yet other embodiments, the first portion (a) and the second portion (b) are immediately adjacent to each other with no spacer sequence in between. Preferably, the upstream detection region is not identical to or complementary to the target sequence targeted by the target sequence binding region; or the upstream detection region should not hybridize with the target sequence under highly stringent conditions.

In some embodiments, the probe comprises a reporter element. Preferably, the reporter element is detectable only after the probe has been hydrolyzed. In some exemplary embodiments, the reporter element comprises a reporter group giving off a detection signal and a quencher group suppressing the detection signal. Exemplary reporter group is preferably a fluorescence group selected from the group consisting of FAM, HEX, VIC, ROX, Cy5, Cy3, and any other suitable fluorescent group known in the art. The quencher group can be selected from the following group consisting of TAMRA, BHQ1, BHQ2, BHQ3, DABCYL, QXL, DDQI, and any other suitable quencher group known in the art.

In some embodiments, the probe does not contain any modified nucleic acid in the mainchain such as MGB, LNA, PNA, BNA, SuperBase, or any other modified nucleic acid known in the art (although modified nucleic acid may be advantageously included in the reporter group and/or the quencher group). It will be understood by those skilled in that art that for cost considerations, probes are preferably selected from commercially available conventional probes with only minimum modifications to the reporter element, the quencher group or both. In a preferred embodiment, the probe is a TaqMan probe. In another preferred embodiment, the reporter is located at the 5' end of the probe and the quencher is located at the 3' end of the probe.

Said nucleic acid sequence variation to be detected can be one or more selected from the group consisting of a base substitution, an insertion, a deletion, and an inversion. In some embodiments, the sequence variation is a base substitution, i.e., there is no difference in the number of bases between the two target sequences to be detected (e.g., the wild type and the mutant type), yet one or more bases are different in type (such as A, T, G, C). In some implementations, the sequence variation is a point mutation, i.e., only one base is different in type.

The length of the first forward primer (F1) is preferably between 50-120 bases, and more preferably between 60-90 bases. In some embodiments, the $T_m$ value of the target sequence binding region of the first forward primer can be 40° C.-90° C., preferably 50° C.-80° C., and the GC content can be 30%-80%.

The length of the second forward primer (F2) is preferably between 10-40 bases, and more preferably between 14-30 bases. In some embodiments, the $T_m$ value of the second forward primer is between 35° C.-85° C., more preferably between 45° C.-75° C., and the GC content is preferably between 30%-80%.

The length of the probe is preferably between 12-30 bases. In some embodiments, the $T_m$ value of the probe is preferably between 55° C.-75° C., and the GC content preferably between 40%-80%.

The length of the reverse primer (R) is preferably between 15-30 bases. In some embodiments, the $T_m$ value of the reverse primer is preferably between 55° C.-75° C., and the GC content is preferably between 40%-80%.

In a second aspect, the present disclosure further provides a method for detecting a sequence variation of a target nucleic acid using digital PCR enabled by primers substantially as described in the first aspect above.

Methods in accordance with this aspect of the disclosure will generally include applying the following steps to one or more reaction mixture droplets containing a sample to be analyzed, a forward primer (F1), a reverse primer (R), and a probe (P):

allowing the forward primer(s), the reverse primer(s), and the probes to form pre-amplification reaction complexes;

initiating amplification reaction using a second forward primer (F2); and detecting signals emitted by the probes from the amplified reactions, wherein said forward primer(s), reverse primer(s) and probe(s) are substantially the same as described in the first aspect above.

In some embodiments, a digital PCR method in accordance with this aspect of the disclosure may optionally include a step of providing a reaction mixture as described above prior to performing the pre-amplification, amplification, and detection steps.

In an exemplary embodiment, a method in accordance with this aspect of the disclosure may include the steps of:

(i) providing a nucleic acid sample containing the target nucleic acid to be detected, wherein the nucleic acid sample is diluted to a limit and distributed randomly to 770-10,000,000 units for a simultaneous amplification across all units in a uniform thermal cycle;

(ii) performing a pre-amplification on the nucleic acid sample at a first annealing temperature with a first forward primer (F1) and a reverse primer (R) as primers to obtain pre-amplified products.

(iii) performing an amplification on the pre-amplified products at a second annealing temperature, using a second forward primer (F2), the reverse primer, and a probe (P), wherein the probe comprises a reporting group; and (iv) detecting signals released from the reporter group and quantifying the target nucleic acid in the sample based on the signals.

In accordance with embodiments of the present disclosure, the reporter group of the probe is detectable only after the probe is hydrolyzed.

Furthermore, the first forward primer (F1), the second forward primer (F2), the reverse primer (R), and the probe (P) can be based on any one of the embodiments as described above in the first aspect of the disclosure.

Specifically, the first forward primer includes an upstream detection region and a target sequence binding region from a 5' end to a 3' end, respectively. In the pair of digital PCR primers, the following are configured:

(1) The 3' end of the target sequence binding region has an amplification determinant site, which sequentially complements the mutation detection site on the target sequence, and a mismatch region containing one or more bases that are not sequentially complementary to the target sequence is arranged at an upstream of amplification determinant sites; and (2) The upstream detection region comprises, in a direction from a 5' end to a 3' end thereof: a portion (a) having a same sequence as the second forward primer, and a portion (b) having a same sequence as the probe.

As describe in the first aspect above, the reverse primer (R) can be a conventional primer that sequentially complements a sequence downstream of the mutation detection site on the target sequence. As such, the reverse primer (R) can be designed by a conventional technique known to people of ordinary skills in the field, based on the principle of complementary pairing of bases. Preferably, a same reverse primer can be employed in each of the above steps (i) and (ii). More preferably, the complementary region between the reverse primer and the target sequence can be arranged around 50-200 bp downstream of a complementary region between the forward primer and the target sequence. It is noted that in some embodiments, naming of the forward primers and the reverse primers can be interchanged if the sense and antisense chains are switched.

In some embodiments, the first annealing temperature and the second annealing temperature can be different. In some embodiments, the $T_m$ value of the first forward primer (F1) is different from that of the second forward primer (F2). In some preferred embodiments, the $T_m$ value of the first forward primer (F1) is higher than the $T_m$ value of the second forward primer (F2). More preferably, the $T_m$ value of the target sequence binding region of the first forward primer (F1) is higher than that of the second forward primer (F2) by 5-20° C., and more preferably by 10-15° C.

In the first forward primer (F1), a length of the mismatch region within the target sequence binding region can be ~1-15 bases, such as 1, 2, 3, 4, 5, 6, 7, 8, 9, 10, 11, 12, 13, 14 or 15 bases. In the first forward primer, a distance between the amplification determinant site and the mismatch region can be ~0-20 bases. According to some embodiments of the first forward primer, the 3' end of the amplification determinant site is the 3' end of the first forward primer; in other words, the amplification determinant site is located at the very 3' end of the first forward primer, and there are no other bases downstream of the site. According to some other embodiments of the first forward primer, there are ~1-10 bases downstream of the amplification determinant site.

According to some embodiments of the first forward primer, one or more bases are spaced between the portion (a) and the portion (b) of the upstream detection region. Yet in other embodiments, there is no other base spaced between the portion (a) and the portion (b) of the upstream detection region. Preferably, the upstream detection region is configured not to sequentially match or complement with the target sequence, or to hybridize with the target sequence under a strict condition.

In some embodiments, the probe comprises a reporting group and a quenching group. Herein, the reporting group can be a fluorescence group selected from the following group: FAM, HEX, VIC, ROX, Cy5, Cy3, and other suitable fluorescence group known in the art. The quenching group can be selected from the following group: TAMRA, BHQ1, BHQ2, BHQ3, DABCYL, QXL, DDQI, or a suitable quenching group known in the art. In some embodiments, the probe has no other modification such as MGB, LNA, PNA, BNA, SuperBase, etc. In a preferred embodiment, the probe of the present disclosure is TaqMan probe. In a preferred embodiment, the reporting group is located at the 5' end of the probe and the quenching group is located at the 3' end of the probe.

In any of the embodiments of the first forward primer, the sequence variation can be one or more of the following types: a base substitution, an insertion, a deletion, and an inversion. In some embodiments, sequence variation is a base substitution, i.e., there is no difference in the number of bases between the two target sequences to be detected (e.g., the wild type and the mutant type), yet one or more bases are different in type (i.e., A, T, G, C). In some implementations, the sequence variation is a point mutation, i.e., only one base is different in type.

In some embodiments, only one first forward primer is used in a reaction system. For example, the reaction system is only specific for the mutant target sequence, or only specific for the wild type target sequence.

In some other embodiments, simultaneous determination of wildtype and mutant target sequences, or for simultaneous determination of multiple mutant target sequences is contemplated. In these embodiments, multiple (e.g., two or more) first forward primers (F1) (e.g., multiple first forward primers in a same reaction unit) and multiple (e.g., two or more) probes (e.g., multiple probes in a same reaction unit) are used in the same reaction system. Preferably, the multiple first forward primers, have different amplification determinant sites, and the second portion (b) within the upstream detection region is different; the multiple probes may each have a different sequence and reporter. The first portion (a) of the upstream detection region may also be different. For example, the method can be used for simultaneous assay of wild type and mutant target sequences, or for simultaneous assay of multiple mutant target sequences. In embodiments using multiple first forward primers, different first forward primers can share a same reverse primer.

The length of the first forward primer can be 50-120 bases, and preferably 60-90 bases. In some embodiments, the $T_m$ value of the target sequence binding region of the first forward primer can be 40° C.-90° C., preferably 50° C.-80° C., and the GC content can be 30%-80%. The length of the second forward primer can be 10-40 bases, and preferably 14-30 bases. In some embodiments, the $T_m$ value of the second forward primer can be 35° C.-85° C., preferably 45° C.-75° C., and the GC content can be 30%-80%. The length of the probe can be 12-30 bases. In some embodiments, the $T_m$ value of the probe can be 55° C.-75° C., and the GC content can be 40%-80%. The length of the reverse primer can be 15-30 bases. In some embodiments, the $T_m$ value of the reverse primer can be 55° C.-75° C., and the GC content can be 40%-80%.

According to some embodiments, the number of cycles for pre-amplification (i.e., step (ii)) using the F1 primer and the R primer is 3-10 cycles, and more preferably 5-8 cycles. In some embodiments, the cycle number of the amplification (i.e., step (iii)) using F2 primers and probe P and the R primer is 35-50 cycles, and more preferably 40-45 cycles.

According to some embodiments, annealing temperatures suitable for forming the pre-amplification complexes is higher than that for the amplification reactions by about 5-20° C., and more preferably by 10-15° C.

Procedures and common reaction conditions (e.g., denaturation temperature, time, etc.) for performing digital PCR are well-known in the art (Molecular Cloning: A Laboratory Manual (Fourth Edition), ISBN 978-1-936113-42-2, provides detailed description of procedures and common reaction conditions, the entire content of which is incorporated herein by reference). For example, in some exemplary embodiments, the specific amplification reaction conditions in step (ii) and step (iii) may be: pre-denaturation at 92-96° C. for 5-15 minutes; denaturation at 92-95° C. for 10-60 seconds and annealing and extending at 55-75° C. for 30-90 seconds, for 3-10 cycles; denaturation at 92-95° C. for 10-60 seconds and annealing and extending at 45-65° C. for 30-90 seconds, for 35-50 cycles; inactivation at 94-98° C. for 5-15 minutes; and terminating the PCR reaction at 4-15° C.

Determination of the optimal amount of primers and probes to use in the reaction system can be determined by conventional experiments known in the art. Such information is well within the skill of the art and does not require repeating here.

As an illustrative example, a suitable concentration for the first forward primer (F1) may be 15 nM-150 nM; a suitable concentration for the second forward primer may be 150 nM-1500 nM; a suitable concentration for the probe (P) may be 50 nM-800 nM; and a suitable concentration for the reverse primer (R) may be 150 nM-1800 nM.

In some preferred embodiments, the concentration of the first forward primer (F1) is 30 nM-60 nM; the concentration for the second forward primer (F2) is 300 nM-600 nM, the concentration for the probe (P) is 150 nM-400 nM, and the concentration for the reverse primer (R) is 300 nM-900 nM.

Detection of signals from the probes substantially mirrors detection methods used for TaqMan probes, which utilizes the 5'-exonuclease activity of the Taq enzyme to cleave a fluorescence reporter-labelled oligonucleotide probe that binds to a target sequence during amplification. Because of the specific binding between the probe and the template, in the digital PCR reaction, the number of droplets emitting fluorescent signals represents the number of templates in the reaction system. Finally, the concentration of templates can be obtained by means of Poisson correction. In those embodiments where TaqMan probes are used as the fluorescent signal generation method, the design method of the probe is the same as that of a convention PCR.

In some embodiments, samples containing analyte such as target nucleic acids may be obtained from biological sources, such as biological fluids, living tissues, frozen tissues, paraffin sections, etc. In some preferred embodiments, the samples include peripheral blood, urine, lavage fluid, cerebrospinal fluid, feces, saliva, or any other biological samples amenable to such analysis.

In the third aspect, the present disclosure further provides a kit for digital PCR, comprising one or more first forward primer (F1), a second forward primer (F2), a reverse primer (R) and a probe (P). Each of the one or more first forward primer comprises in 5' to 3' order an upstream detection region and a target sequence binding region from a 5' end to a 3' end, respectively, wherein:

(1) The 3' end of the target sequence binding region has an amplification determinant site, which is complementary to the mutation detection site on the target sequence, and a mismatch region containing one or more bases that are not sequentially complementary to the target sequence is arranged at an upstream of the amplification determinant site; and (2) The upstream detection region comprises, in 5' to 3' order, a portion (a) having a same sequence as the second forward primer, and a portion (b) having a same sequence as the probe.

In some embodiments in accordance with this aspect of the disclosure, the kit may further include instructions for performing a digital PCR method substantially as described in the second aspect above.

The reverse primer can be a conventional primer that sequentially complements a sequence downstream of the mutation detection site on the target sequence. As such, the reverse primer can be designed by a conventional technique known to people of ordinary skills in the field, based on the principle of complementary pairing of bases. Preferably, a same reverse primer can be employed in each of the above steps (i) and (ii). More preferably, the complementary region between the reverse primer and the target sequence can be arranged around 0-200 bp (e.g., 0-100 bp, or 0-50 bp) downstream of a complementary region between the forward primer and the target sequence. It is noted that in some embodiments, naming of the forward primers and the reverse primers can be interchanged if the sense and antisense chains are switched.

In some embodiments, the $T_m$ value of each first forward primer is different from that of the second forward primer. In some preferred embodiments, the $T_m$ value of each first forward primer is higher than the $T_m$ value of the second forward primer. More preferably, the $T_m$ value of the target sequence binding region of each first forward primer is higher than that of the second forward primer by 5-20° C., and more preferably by 10-15° C.

In each first forward primer, a length of the mismatch region within the target sequence binding region can be ~1-15 bases, such as 1, 2, 3, 4, 5, 6, 7, 8, 9, 10, 11, 12, 13, 14 or 15 bases. In each first forward primer, a distance between the amplification determinant site and the mismatch region can be ~0-20 bases. According to some embodiments, in each first forward primer, the 3' end of the amplification determinant site is the 3' end of each first forward primer; in other words, the amplification determinant site is located at the very 3' end of each first forward primer, and there are no other bases downstream of the site. According to some other embodiments, in each first forward primer, there are ~1-10 bases downstream of the amplification determinant site.

According to some embodiments, in each first forward primer, one or more bases are spaced between the portion (a) and the portion (b) of the upstream detection region. Yet in other embodiments, there is no other base spaced between the portion (a) and the portion (b) of the upstream detection region. Preferably, the upstream detection region is configured not to sequentially match or complement with the target sequence, or to hybridize with the target sequence under a strict condition.

In some embodiments, the probe comprises a reporter and a quenching group. Herein, the reporter can be a fluorescence group selected from the following group: FAM, HEX, VIC, ROX, Cy5, Cy3, and other suitable fluorescence group known in the art. The quenching group can be selected from the following group: TAMRA, BHQ1, BHQ2, BHQ3, DABCYL, QXL, DDQI, and other suitable quenching group(s) known in the art. In some embodiments, the probe contains no other modification such as MGB, LNA, PNA, BNA, SuperBase, etc. In a preferred embodiment, the probe of the present disclosure is TaqMan probe. In a preferred embodiment, the reporter is located at the 5' end of the probe and the quenching group is located at the 3' end of the probe.

In any of the embodiments of the first forward primer, the sequence variation can be one or more of the following types: a base substitution, an insertion, a deletion, and an inversion. In some embodiments, sequence variation is a base substitution, i.e., there is no difference in the number of bases between the two target sequences to be detected (e.g., the wild type and the mutant type), yet one or more bases are different in type (i.e., A, T, G, C). In some implementations, the sequence variation is a point mutation, i.e., only one base is different in type.

The length of each first forward primer can be 50-120 bases, and preferably 60-90 bases. In some embodiments, the $T_m$ value of the target sequence binding region of each first forward primer can be 40° C.-90° C., preferably 50° C.-80° C., and the GC content can be 30%-80%. The length of the second forward primer can be 10-40 bases, and preferably 14-30 bases. In some embodiments, the $T_m$ value of the second forward primer can be 35° C.-85° C., preferably 45° C.-75° C., and the GC content can be 30%-80%. The length of the probe can be 12-30 bases. In some embodiments, the $T_m$ value of the probe can be 55° C.-75° C., and the GC content can be 40%-80%. The length of the reverse primer can be 15-30 bases. In some embodiments, the $T_m$ value of the reverse primer can be 55° C.-75° C., and the GC content can be 40%-80%.

In a forth aspect, the present disclosure further provides a digital PCR kit useful for detecting sequence variation of a nucleic acid. The digital PCR kit substantially comprises the composition according to any one of the embodiments as described above in the third aspect.

According to some embodiments, the digital PCR kit is configured to specifically detect mutations of tumor-related genes. In some embodiments, the type of the sequence variation is a point mutation.

According to some embodiments, the digital PCR kit further includes a reaction buffer, a positive control, a negative control and/or a blank control. In some embodiments of the digital PCR kit, the reaction buffer contains KCl, MgCl2, Tris-HCl, DTT, various dNTPs and a DNA polymerase.

In a fifth aspect, the present disclosure further provides methods for diagnosing, or evaluating a risk, for a disease associated with a sequence variation in a subject.

Methods in accordance with this aspect of the disclosure will generally be applying a series of method steps to a biological sample containing a target nucleic acid, said sample is diluted to a pre-determined level and distributed randomly to 770-10,000,000 fractions in the form of microdroplets, each droplets containing a reaction mixture comprising one or more first forward primer(s) (F1), one or more second forward primer(s) (F2), one or more reverse primer(s) (R) and one or more probe(s) (P). The forward primer(s), reverse primer(s), and probe(s) are substantially as described in the first aspect. Method steps in accordance with this aspect of the disclosure generally include:
   maintaining a uniform reaction condition to allow the reaction mixtures in each droplet to form pre-amplification complexes;
   initiating amplification reactions on the pre-amplification complexes;
   detecting signals emitted from the probes in each droplet;
   analyzing the signals to determine a characteristic information about the target nucleic acid; and
   determining a diagnostic or risk assessment for the subject based on the characteristic information of the target nucleic acid.

In some preferred embodiment, methods in accordance with this aspect of the disclosure comprises the following steps:
   (i) obtaining a nucleic acid sample containing a target nucleic acid to be detected from the subject, wherein the nucleic acid of the sample is diluted to a limit by limiting dilution and distributed randomly to 770-10,000,000 units for a simultaneous amplification across all units in a uniform thermal cycle;
   (ii) performing a pre-amplification on the nucleic acid sample at a first annealing temperature using a first forward primer (F1) and a reverse primer (R) as primers to obtain pre-amplified products.
   (iii) performing an amplification on the pre-amplified products at a second annealing temperature, using a second forward primer (F2), the reverse primer, and a probe (P), wherein the probe comprises a reporting group reporter;
   (iv) detecting signals released from the reporting group reporter and quantifying the target nucleic acid in the sample based on the signals; and
   (v) determining whether or not the subject has, or carries a risk for, the disease based on a result of quantification in step (iv).

According to some embodiments of the kit, the reverse primer can be a conventional primer that sequentially complements is complementary to a sequence downstream of the mutation detection site on the target sequence. As such, the reverse primer can be designed by a conventional technique known to people of ordinary skills in the art, based on the principle of complementary pairing of bases. Preferably, a same reverse primer can be employed in each of the above steps (i) and (ii). More preferably, the complementary region between the reverse primer and the target sequence can be arranged around 50-200 bp downstream of a complementary region between the forward primer and the target sequence. It is noted that in some embodiments, naming of the forward primers and the reverse primers can be interchanged if the sense and antisense chains are switched.

In some embodiments, the first annealing temperature and the second annealing temperature can be different. In some embodiments, the $T_m$ value of the first forward primer is different from that of the second forward primer. In some preferred embodiments, the $T_m$ value of the first forward primer is higher than the $T_m$ value of the second forward primer. More preferably, the $T_m$ value of the target sequence binding region of the first forward primer is higher than that of the second forward primer by 5-20° C., and more preferably by 10-15° C.

In some embodiments, in the first forward primer, the length of the mismatch region within the target sequence binding region can be ~1-15 bases, such as 1, 2, 3, 4, 5, 6, 7, 8, 9, 10, 11, 12, 13, 14 or 15 bases. In some embodiments, in the first forward primer, a distance between the amplification determinant site and the mismatch region can be ~0-20 bases. According to some embodiments of the first forward primer, the 3' end of the amplification determinant site is the 3' end of the first forward primer; in other words, the amplification determinant site is located at the very 3' end of the first forward primer, and there are no other bases downstream of the site. According to some other embodiments of the first forward primer, there are ~1-10 bases downstream of the amplification determinant site.

According to some embodiments of the first forward primer, one or more bases are spaced between the portion (a) and the portion (b) of the upstream detection region. Yet in other embodiments, there is no other base spaced between the portion (a) and the portion (b) of the upstream detection region. Preferably, the upstream detection region is not identical to or complementary to configured not to sequentially match or complement with the target sequence, or to hybridizes with the target sequence under highly stringent strict conditions.

In some embodiments, the probe comprises a reporter and a quencher. Herein, the reporting group reporter can be a fluorescence group selected from the following group: FAM, HEX, VIC, ROX, Cy5, Cy3, and other suitable fluorescent groups known in the art. The quencher can be selected from the following group: TAMRA, BHQ1, BHQ2, BHQ3, DABCYL, QXL, DDQI, and other suitable quencher group(s) known in the art. In some embodiments, the probe has no other modification such as MGB, LNA, PNA, BNA, SuperBase, etc. In a preferred embodiment, the probe of the present disclosure is TaqMan probe. In a preferred embodiment, the reporter is located at the 5' end of the probe and the quencher is located at the 3' end of the probe.

In any of the embodiments of the first forward primer, the sequence variation can be one or more selected from the group consisting of: a base substitution, an insertion, a deletion, and an inversion. In some embodiments, the sequence variation is a base substitution, i.e., there is no difference in the number of bases between the two target sequences to be detected (e.g., the wild type and the mutant type), yet one or more bases are different in type (such as A, T, G, C). In some implementations, the sequence variation is a point mutation, i.e., only one base is different in type.

In some embodiments, only one first forward primer is used in a reaction system. For example, the reaction system is only specific for the mutant target sequence, or only specific for the wild type target sequence.

In some other embodiments, multiple (e.g., two or more) first forward primers (e.g., multiple first forward primers in a same reaction unit) and multiple (e.g., two or more) probes (e.g., multiple probes in a same reaction unit) are used in the same reaction system. Preferably, the multiple first forward primers have different amplification determinant sites, and the portion (b) within the upstream detection region is different; the multiple probes have different sequences and reporters; optionally, the portion (a) of the upstream detection region can also be different. For example, the method can be used for simultaneous assay of wild type and mutant target sequences, or for simultaneous assay of multiple mutant target sequences. In embodiments using multiple first forward primers, different first forward primers can share a same reverse primer.

The length of the first forward primer can be 50-120 bases, and preferably 60-90 bases. In some embodiments, the $T_m$ value of the target sequence binding region of the first forward primer can be 40° C.-90° C., preferably 50° C.-80° C., and the GC content can be 30%-80%. The length of the second forward primer can be 10-40 bases, and preferably 14-30 bases. In some embodiments, the $T_m$ value of the second forward primer can be 35° C.-85° C., preferably 45° C.-75° C., and the GC content can be 30%-80%. The length of the probe can be 12-30 bases. In some embodiments, the $T_m$ value of the probe can be 55° C.-75° C., and the GC content can be 40%-80%. The length of the reverse primer can be 15-30 bases. In some embodiments, the $T_m$ value of the reverse primer can be 55° C.-75° C., and the GC content can be 40%-80%.

According to some embodiments, the number of cycles for pre-amplification (i.e., step (ii)) using the F1 primer and the R primer is 3-10 cycles, and more preferably 5-8 cycles. In some embodiments, the cycle number of the amplification (i.e., step (iii)) using F2 primers and probe P is 35-50 cycles, and more preferably 40-45 cycles.

According to some embodiments, the annealing temperature of the pre-amplification (i.e., step (ii)) is higher than that of the amplification (i.e., step (iii)) by about 5-20° C., and more preferably by 10-15° C.

The procedures and common reaction conditions (such as denaturation temperature, time, etc.) for digital PCR amplification are well-known in the art. For example, in some exemplary embodiments, the specific amplification reaction conditions in step (ii) and step (iii) may be: pre-denaturation at 92-96° C. for 5-15 minutes; denaturation at 92-95° C. for 10-60 seconds and annealing and extending at 55-75° C. for 30-90 seconds, for 3-10 cycles; denaturation at 92-95° C. for 10-60 seconds and annealing and extending at 45-65° C. for 30-90 seconds, for 35-50 cycles; inactivation at 94-98° C. for 5-15 minutes; and terminating the PCR reaction at 4-15° C.

The concentration of primers and probes in the reaction system described in the present disclosure can be determined by conventional experiments in the art. In some examples, the concentration of the first forward primer is 15 nM-150 nM, the concentration of the second forward primer is 150 nM-1500 nM, the concentration of the probe P is 50 nM-800 nM, and the concentration of the reverse primer R is 150 nM-1800 nM. In some preferred embodiments, the concentration of the first forward primer is 30 nM-60 nM, the concentration of the second forward primer is 300 nM-600 nM, the concentration of the probe P is 150 nM-400 nM, and the concentration of the reverse primer R is 300 nM-900 nM.

In some embodiments, the samples containing the target nucleic acid sequences may be biological samples, such as biological fluids, living tissues, frozen tissues, paraffin sections, etc. In some preferred embodiments, the samples include peripheral blood, urine, lavage fluid, cerebrospinal fluid, feces, saliva, etc.

In a sixth aspect the present disclosure further provides a method for guiding a medication for a subject with a disease associated with genetic variation Methods in accordance with this aspect of the disclosure will generally be applying a series of method steps to a biological sample of the subject containing a target nucleic acid, said sample is diluted to a pre-determined level and distributed randomly to 770-10,000,000 fractions in the form of micro-droplets, each droplets containing a reaction mixture comprising one or more first forward primer(s) (F1), one or more second forward primer(s) (F2), one or more reverse primer(s) (R) and one or more probe(s) (P). the forward primer(s), reverse primer(s), and probe(s) are substantially as described in the first aspect. Method steps in accordance with this aspect of the disclosure generally include:
   maintaining a uniform reaction condition to allow the reaction mixtures in each droplet to form pre-amplification complexes;
   initiating amplification reactions on the pre-amplification complexes;
   detecting signals emitted from the probes in each droplet;
   analyzing the signals to determine a characteristic information about the target nucleic acid; and
   determining a diagnostic or risk assessment for the subject based on the characteristic information of the target nucleic acid.

In a preferred exemplary embodiment, methods in accordance with this aspect of the disclosure will comprise:
   (vi) performing the steps (i)-(v) as indicated in the method described above in the fifth aspect to determine the genotype of the sequence variation in the subject; and
   (vi): determining a drug regimen based on the genotype of the sequence variation in the subject, wherein the drug regimen is formulated according to the common knowledge of the genotype.

In some embodiments, the use of primers or primers and probe compositions described in any of the embodiments of the present disclosure in preparing kits for diagnosing gene mutation-related diseases is provided. In other implementations, the use of primers or primers and probe compositions described in any of the embodiments of the present disclosure in the preparation of kits for detecting nucleic acid sequence variation is provided.

Methods in accordance with the present disclosure have remarkable advantages in terms of both specificity and sensitivity over prior art methods. Moreover, primer design methods and methods for using primers provided herein will have the further advantages of low cost in addition to providing improved detection accuracy.

BRIEF DESCRIPTION OF THE DRAWINGS

FIG. 1A is a structural diagram of the first forward primer (F1), which comprises an upstream detection region and a target sequence binding region from a 5' end to a 3' end. The 3' end of the target sequence binding region has amplification determinant sites, which sequentially complement the mutation detection sites on the target sequence, and a mismatch region containing one or more bases non-complementary to the target sequence is arranged at an upstream of amplification determinant sites. The upstream detection region comprises, in a direction from a 5' end to a 3' end thereof: a portion (a) having a same sequence as the second forward primer, and a portion (b) having a same sequence as the probe.

FIG. 1B illustrates a working principle of the kit described in the present disclosure. Firstly, the target nucleic acid sequence to be detected is specifically enriched by means of the first forward primer F1 and the reverse primer R, and a sequence complementary to the "upstream detection region" of the first forward primer is added in the enriched product for the subsequent recognition and pairing of the second forward primer F2 and the probe P.

After enrichment of the target nucleic acid template, through a change of an annealing temperature, the second forward primer F2 and the probe P are allowed to recognize the sequence complementary to the upstream detection region of the first forward primer. Then the second forward primer F2 can form a primer pair with the reverse primer R during a template amplification process. The fluorescence signal can be released based on a principle of TaqMan probe hydrolysis.

Figure 1A:
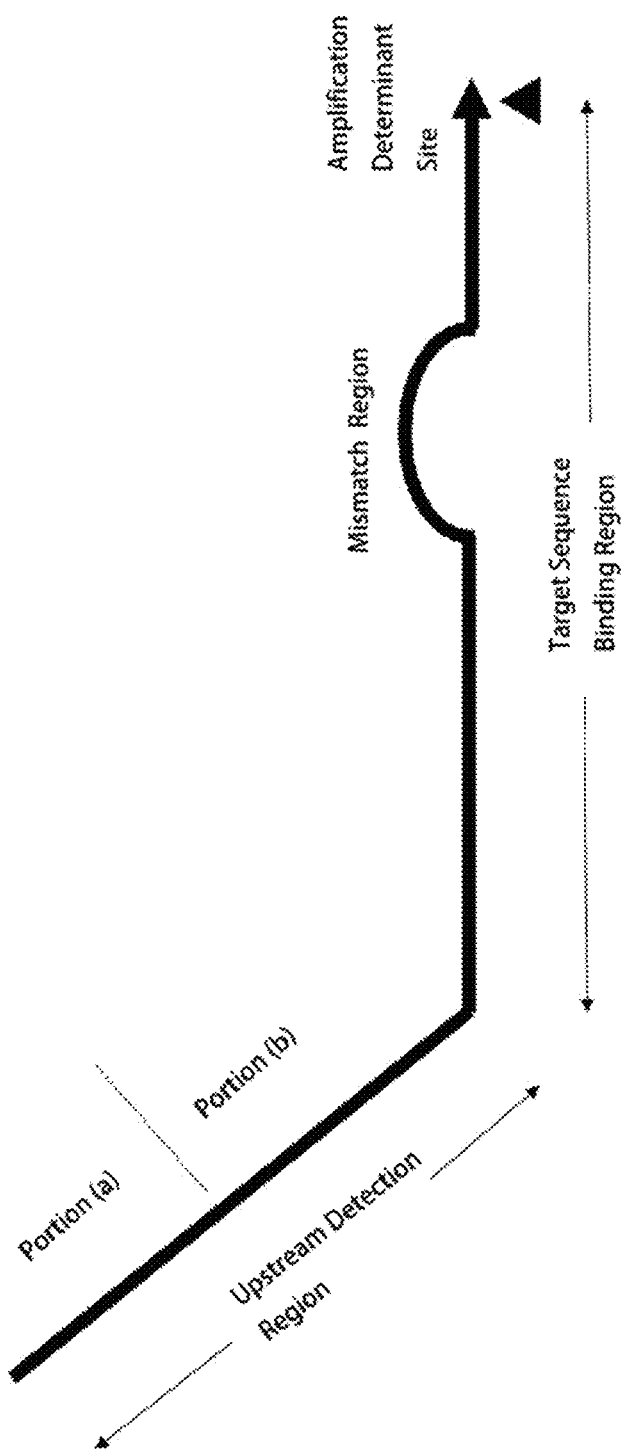
FIG. 1A and FIG. 1B are schematic diagrams of a primer construct according to some embodiments of the disclosure.
Figure 1B:
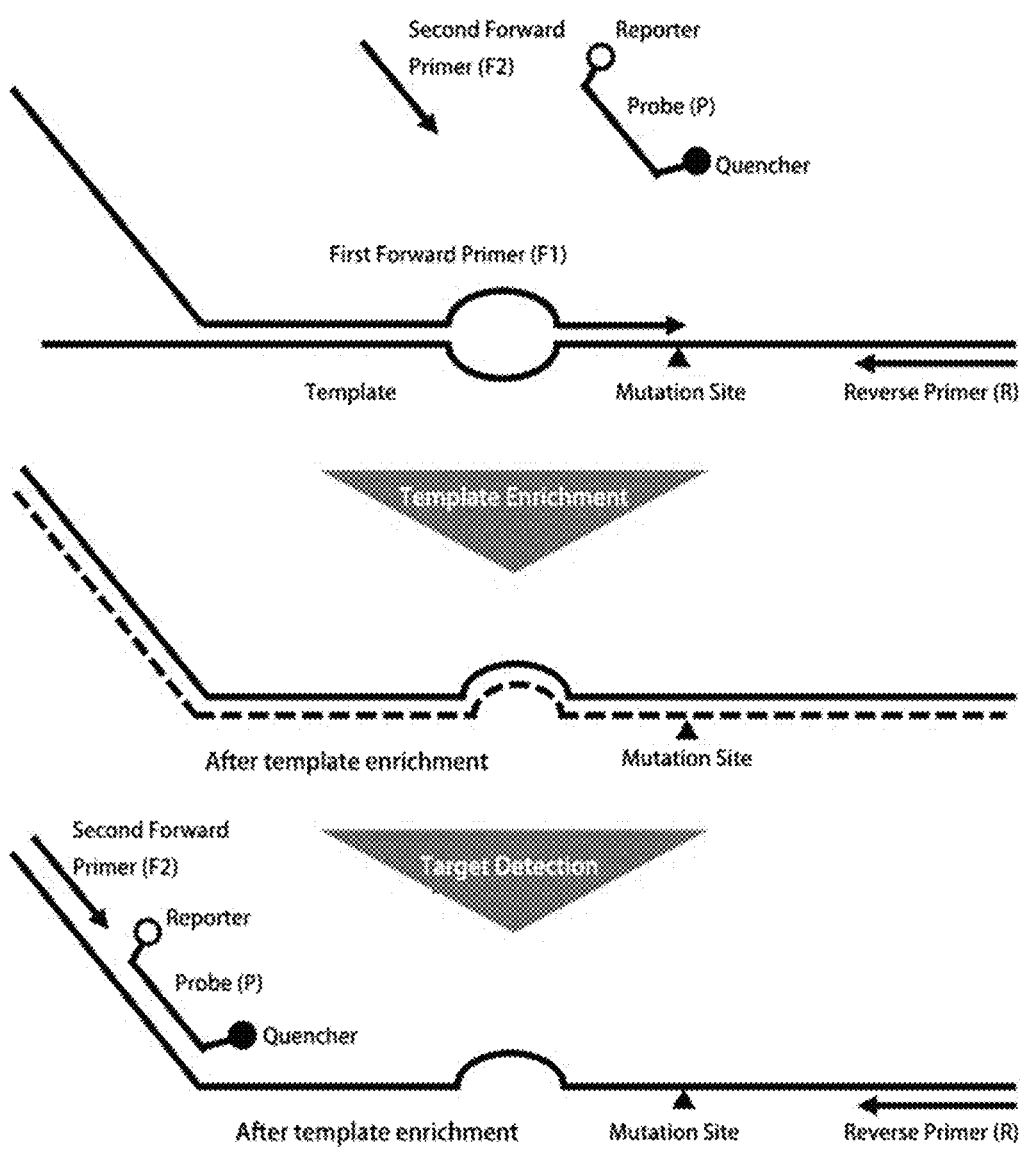
Figure 2:
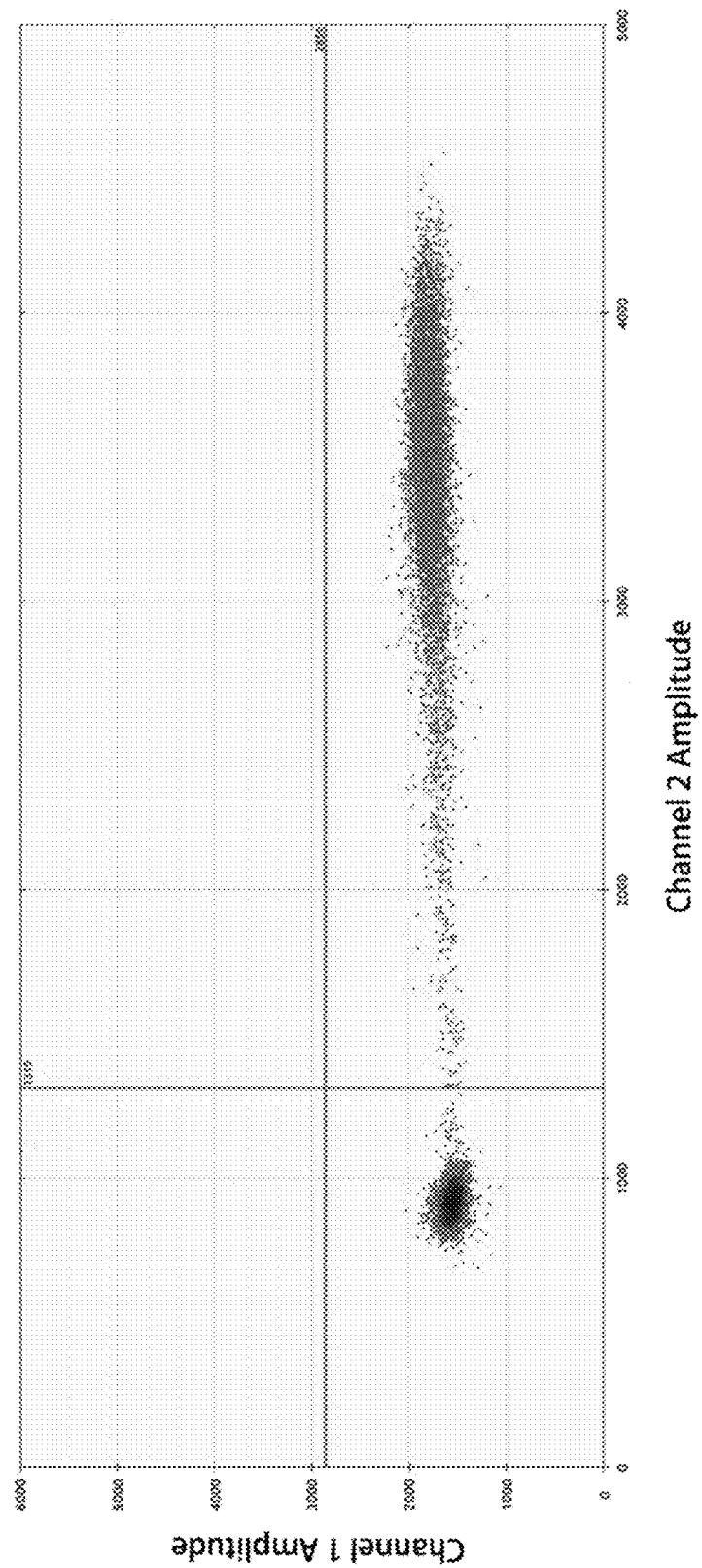
Figure 3:
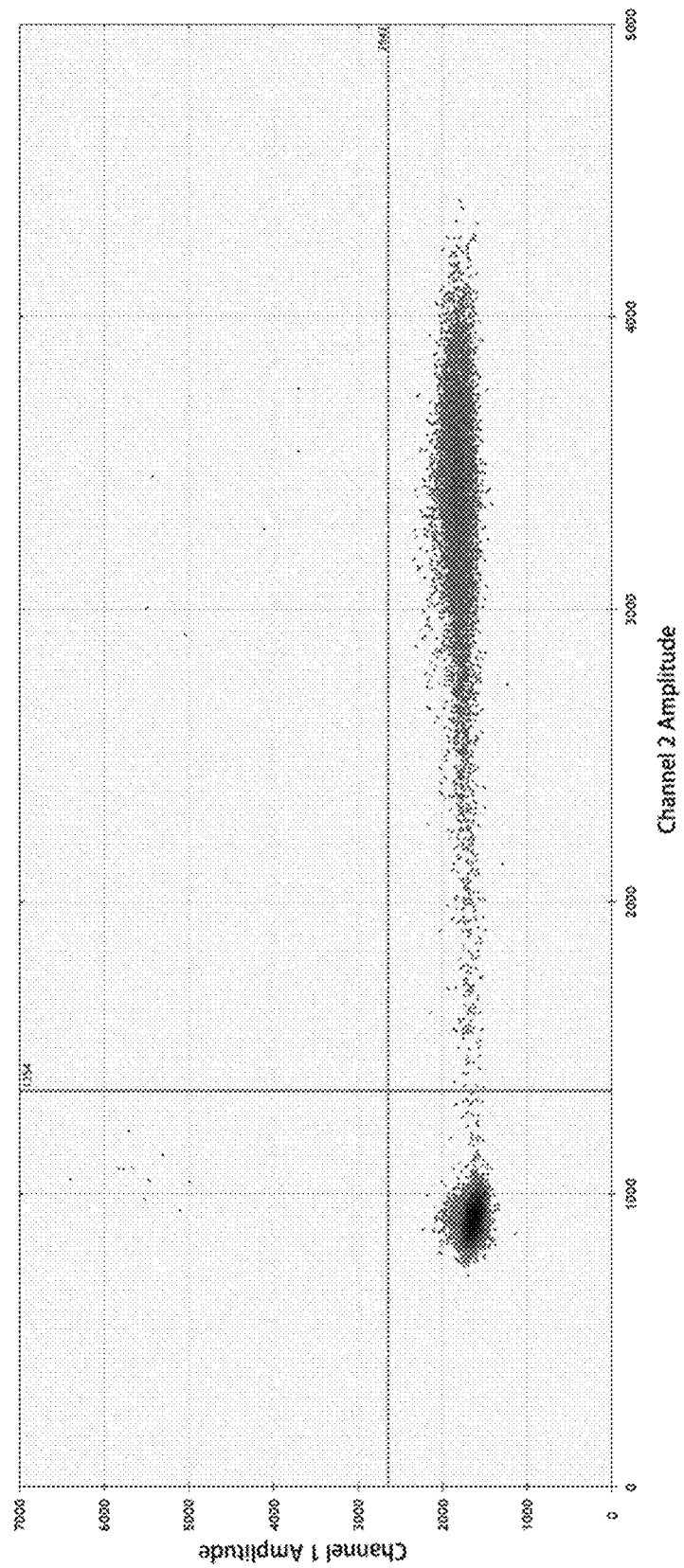

FIG. 2 and FIG. 3 respectively show the results of detecting a point mutation of the BRAF gene by using the primers provided in this disclosure (designed to have one mismatch base). FIG. 2 is a scatter plot of negative samples (i.e., only wild-type genes).

Figure 4A:
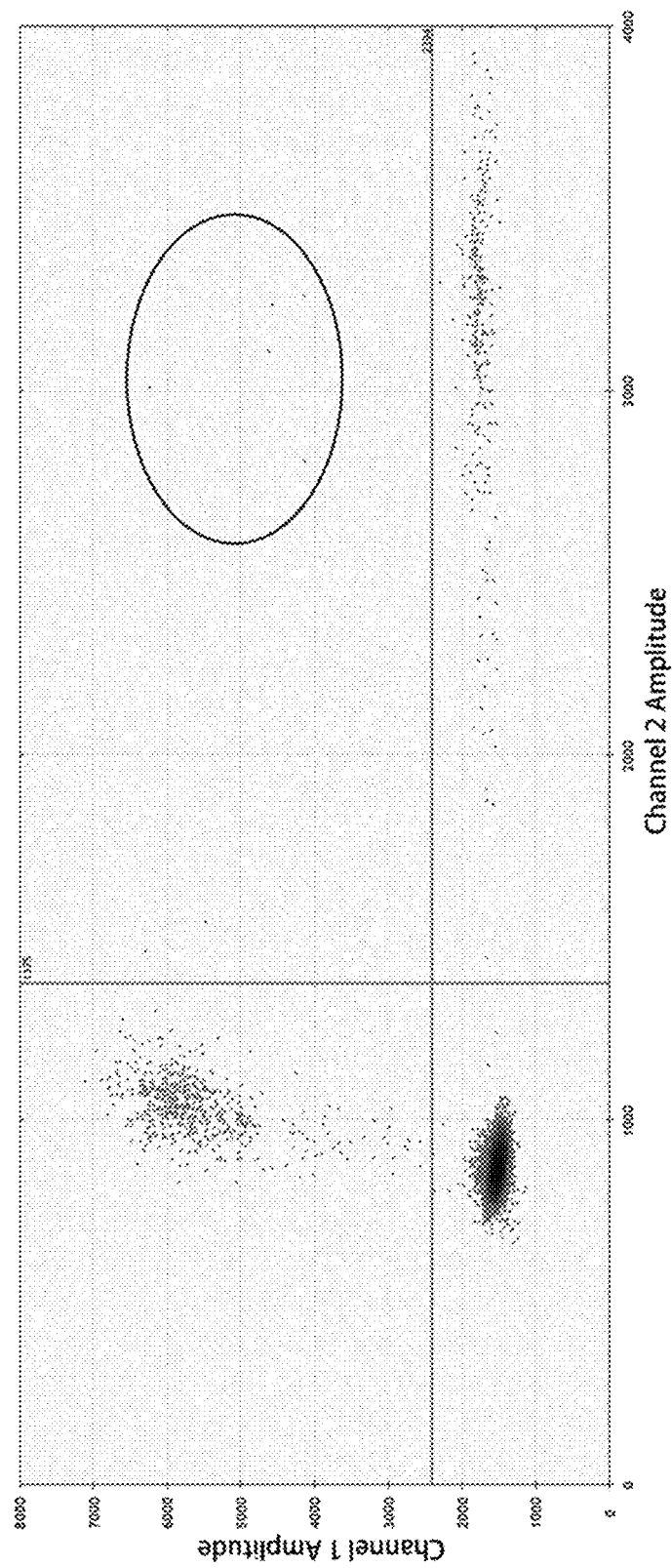
Figure 4B:
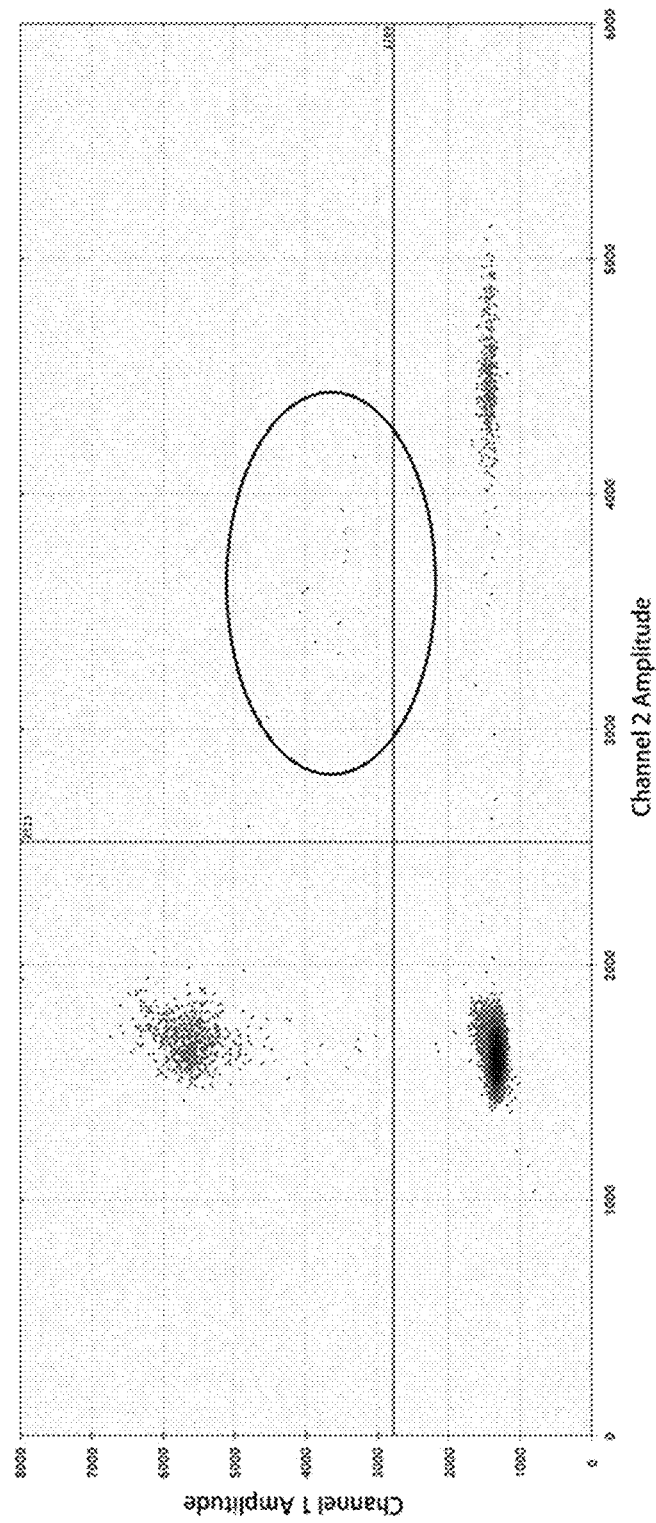

FIG. 3 is a scatter plot of positive samples with theoretical dilution of 0.1%. In both of the scatter plot, the upper left quadrant represents mutant type (i.e., only mutant positive signal), the lower right quadrant represents wild type (i.e., only wild type positive signal), the upper right quadrant represents mutant+wild type (i.e., double positive signal), and the lower left quadrant represents blank (i.e., double negative). Throughout the disclosure, the above quadrant division is applied to all the scatter diagrams FIG. 4A and FIG. 4B show a comparison of BRAF mutation detection results for the same sample using the primer system provided in this disclosure (FIG. 4A) and a comparative kit from Bio-Rad (FIG. 4B). The scatter points in the circle represent wild type+mutant type. It can be seen that the primer system provided in this disclosure has obvious advantages for accurate division of the upper right quadrant and the lower right quadrant.

Figure 5A:
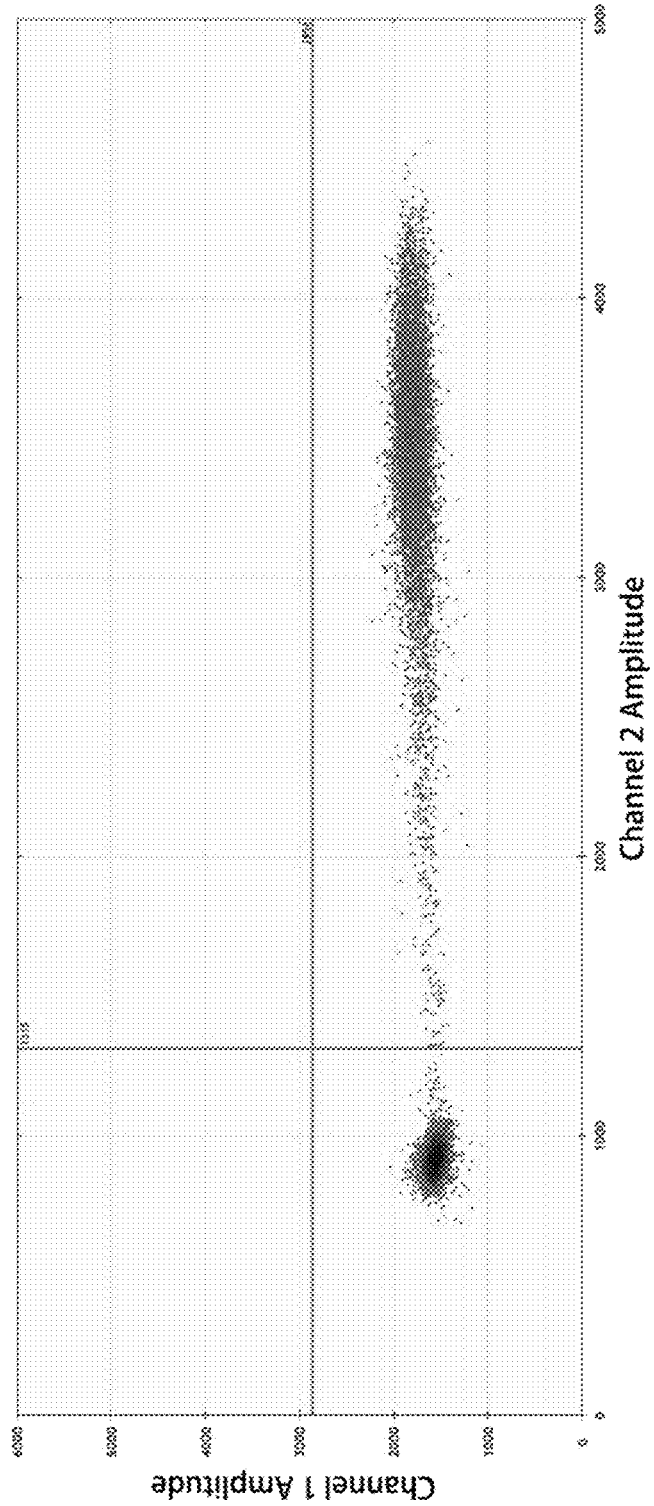
Figure 5B:
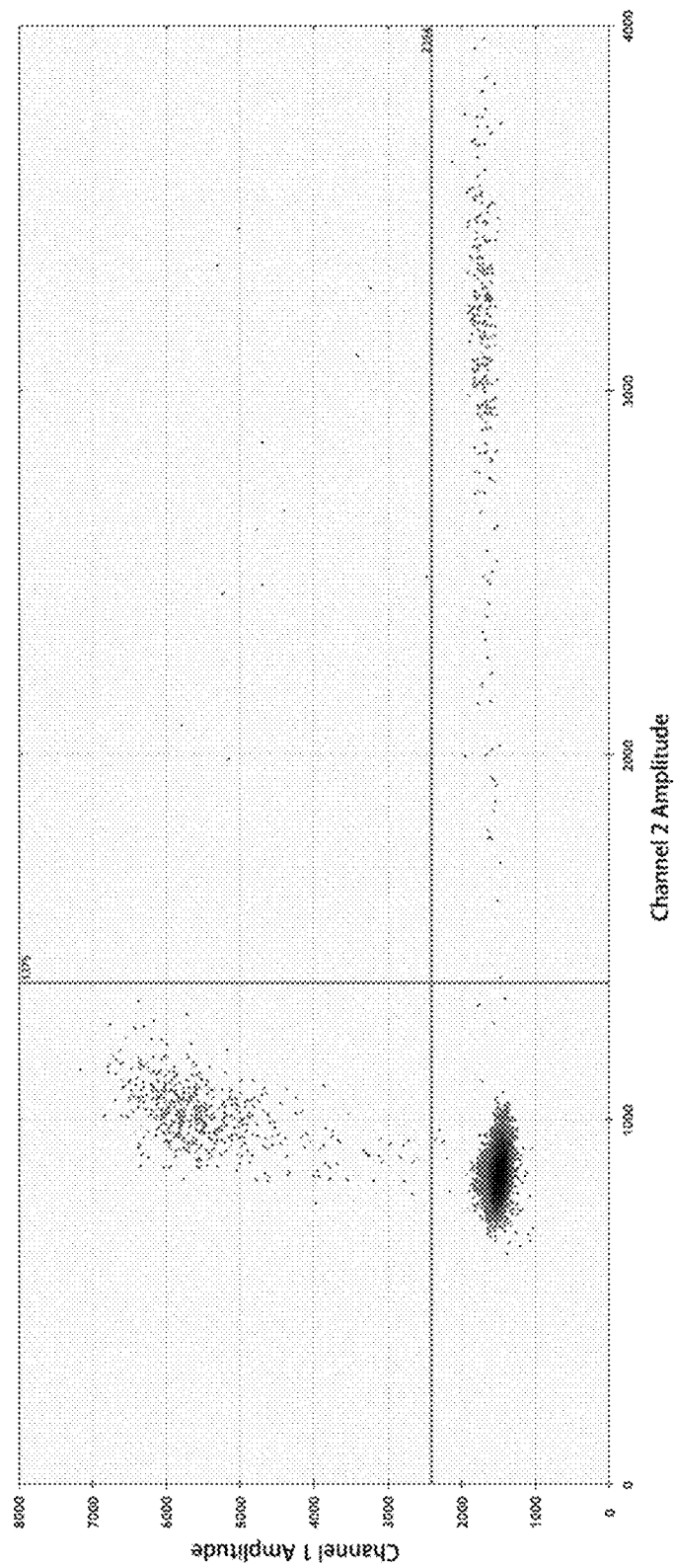

FIG. 5A and FIG. 5B illustrate the detection results of point mutations of BRAF gene using primers designed provided in this disclosure (implicating 14 mismatched bases). FIG. 5A shows a scatter plot for negative samples and FIG. 5B shows a scatter plot for positive samples.

Figure 6A:
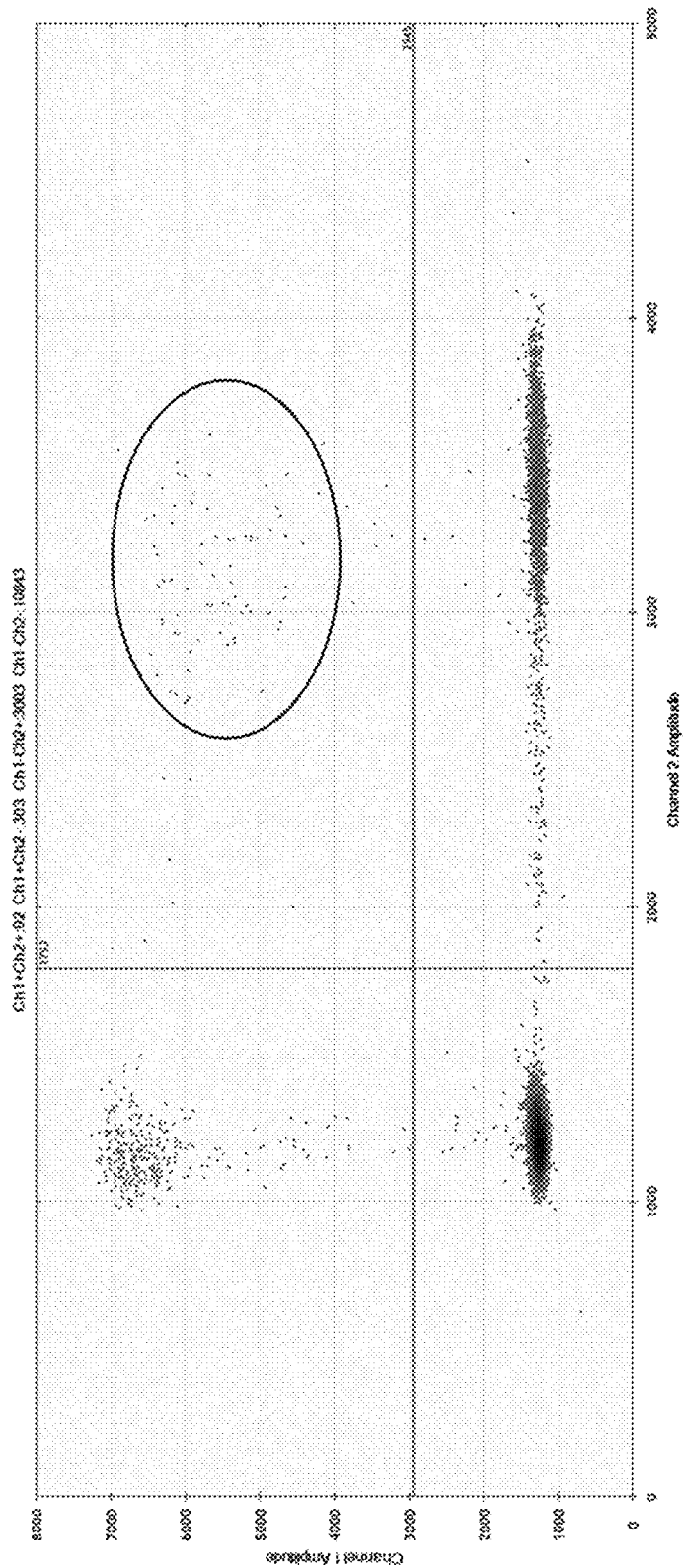
Figure 6B:
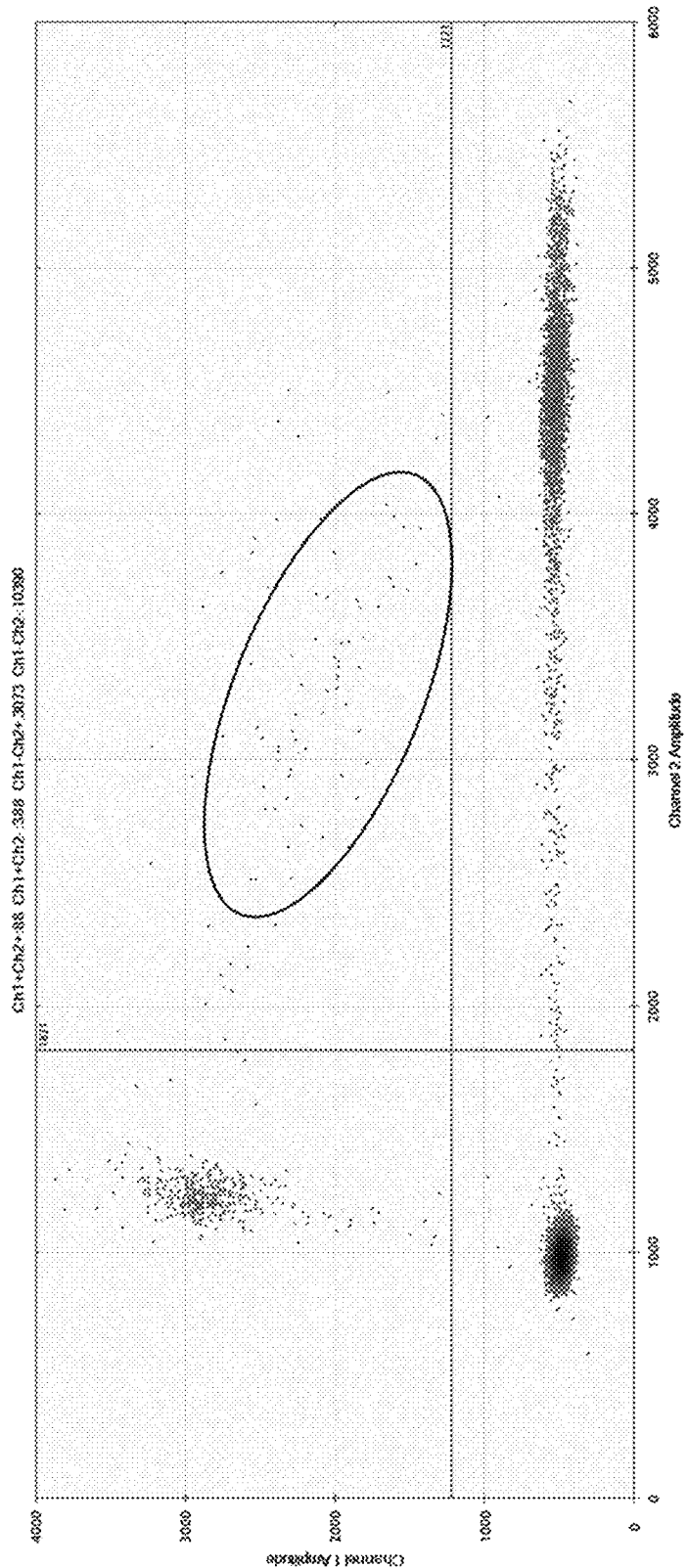

FIG. 6A and FIG. 6B show a comparison of EGFR L858R mutation detection results for the same sample using the primer system provided in this disclosure (FIG. 6A) and a comparative kit from Bio-Rad (FIG. 6B). The scatter points in the circle represent wild type+mutant type. It can be observed that the detection results generated by the primer system provided in this disclosure are more in conformity with the morphological distribution of four quadrants, thus has obvious advantages for accurate threshold setting.

Figure 7A:
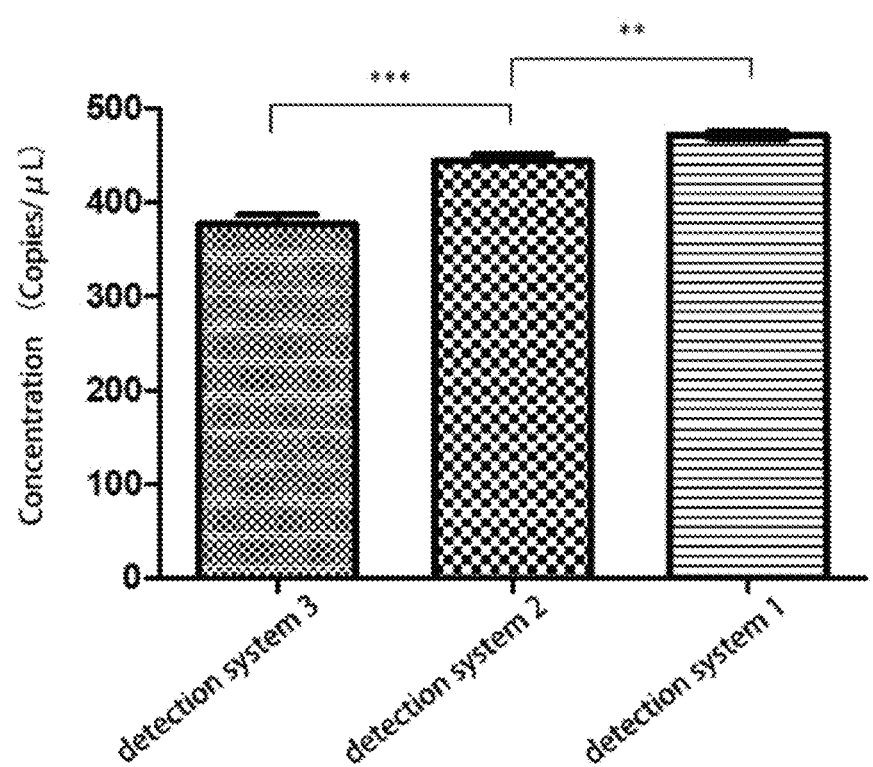
Figure 7B:
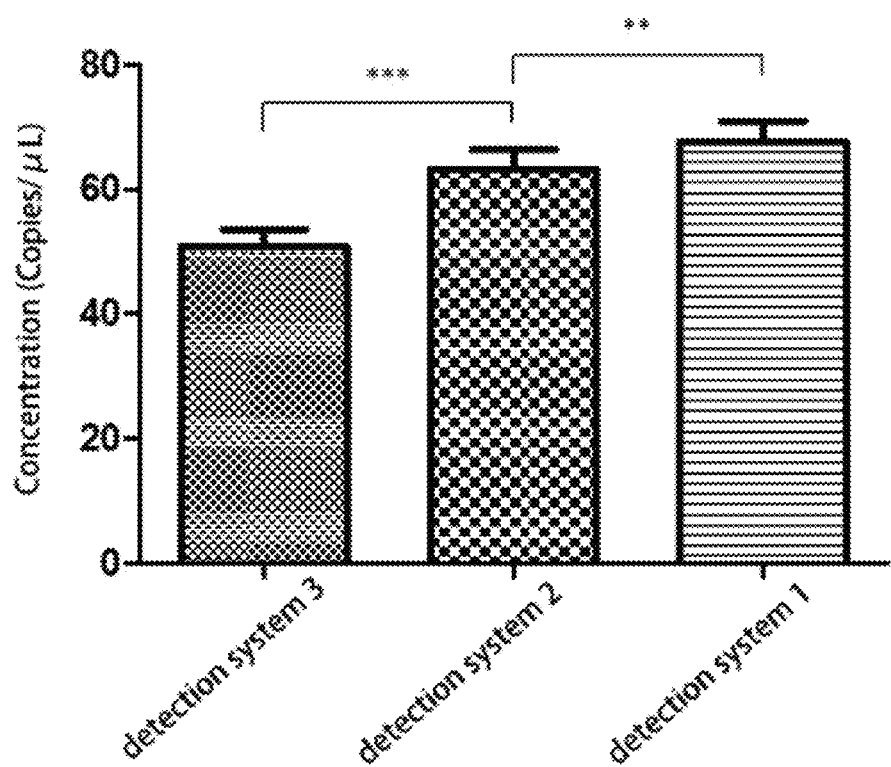
Figure 7C:
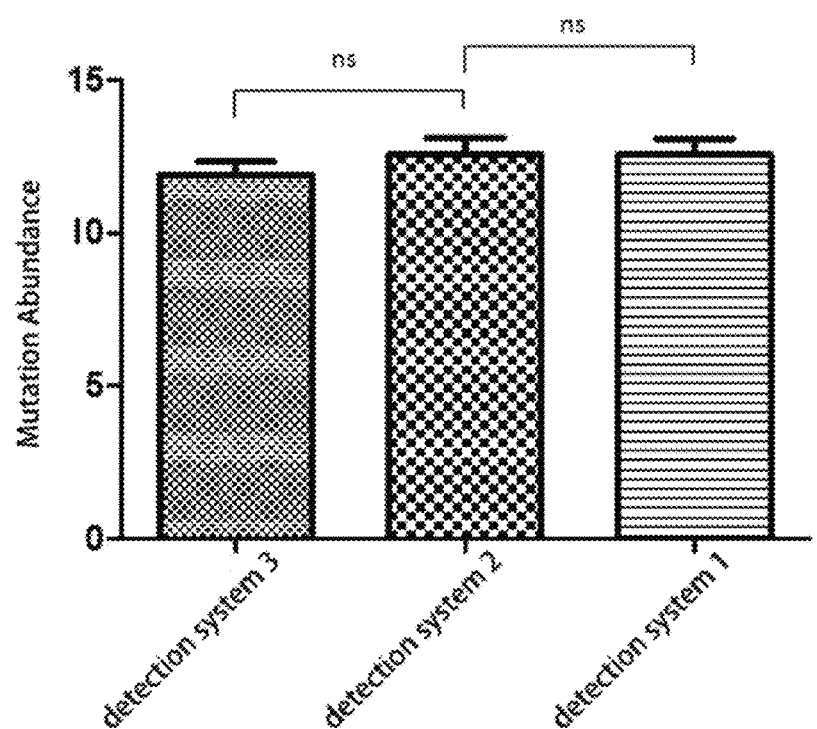

FIG. 7A, FIG. 7B, and FIG. 7C show the data analysis results of the detection results using the EGFR L858R detection system 1, detection system 2 and detection system 3, respectively, over the fragmented DNA samples (having theoretical mutation abundance of ~12%) obtained from the NCI-H1975 cell lines. FIG. 7A shows the quantitative results of the concentrations of the wild-type target nucleic acid sequences; FIG. 7B shows the quantitative results of the concentrations of the mutant target nucleic acid sequences; and FIG. 7C shows the quantitative results of mutant abundance (i.e., mutant concentration/mutant concentration+ wild-type concentration).

Figure 8A:
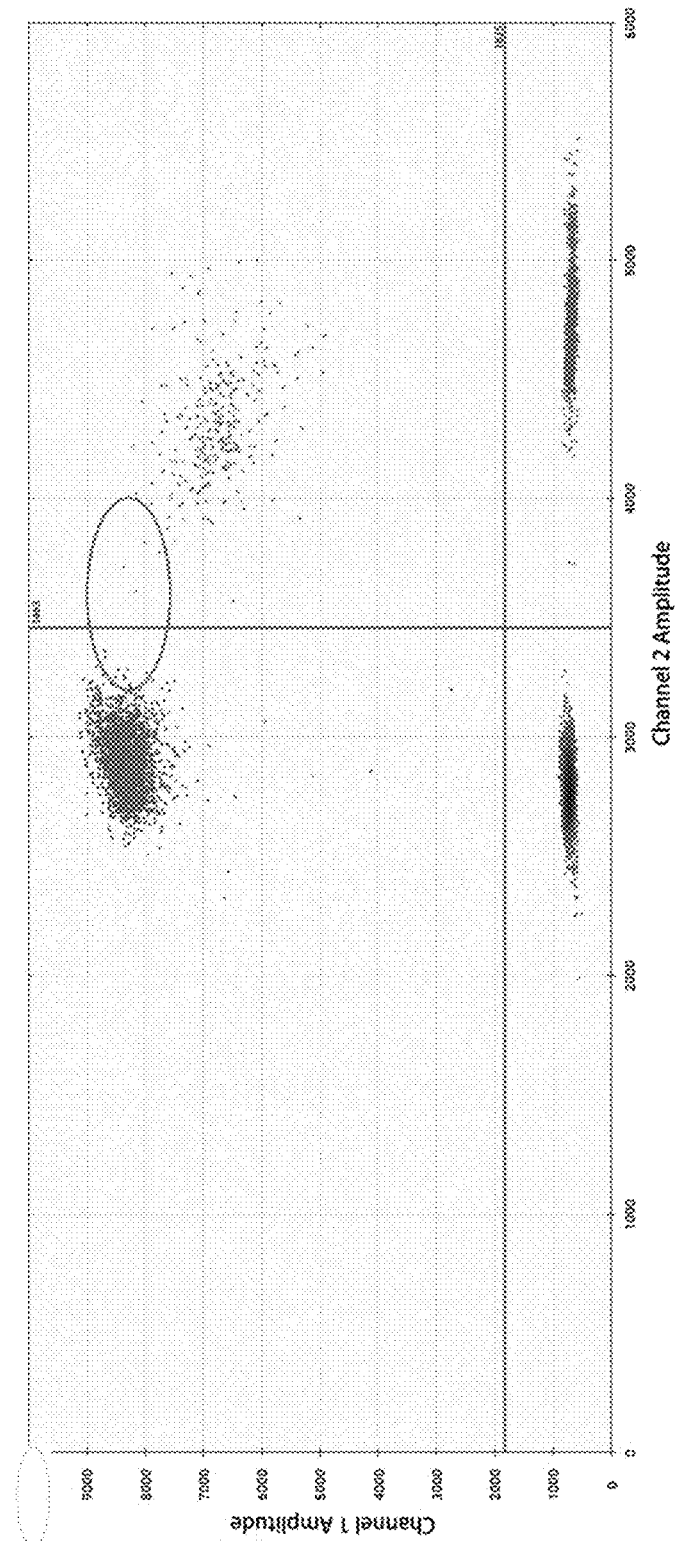
Figure 8B:
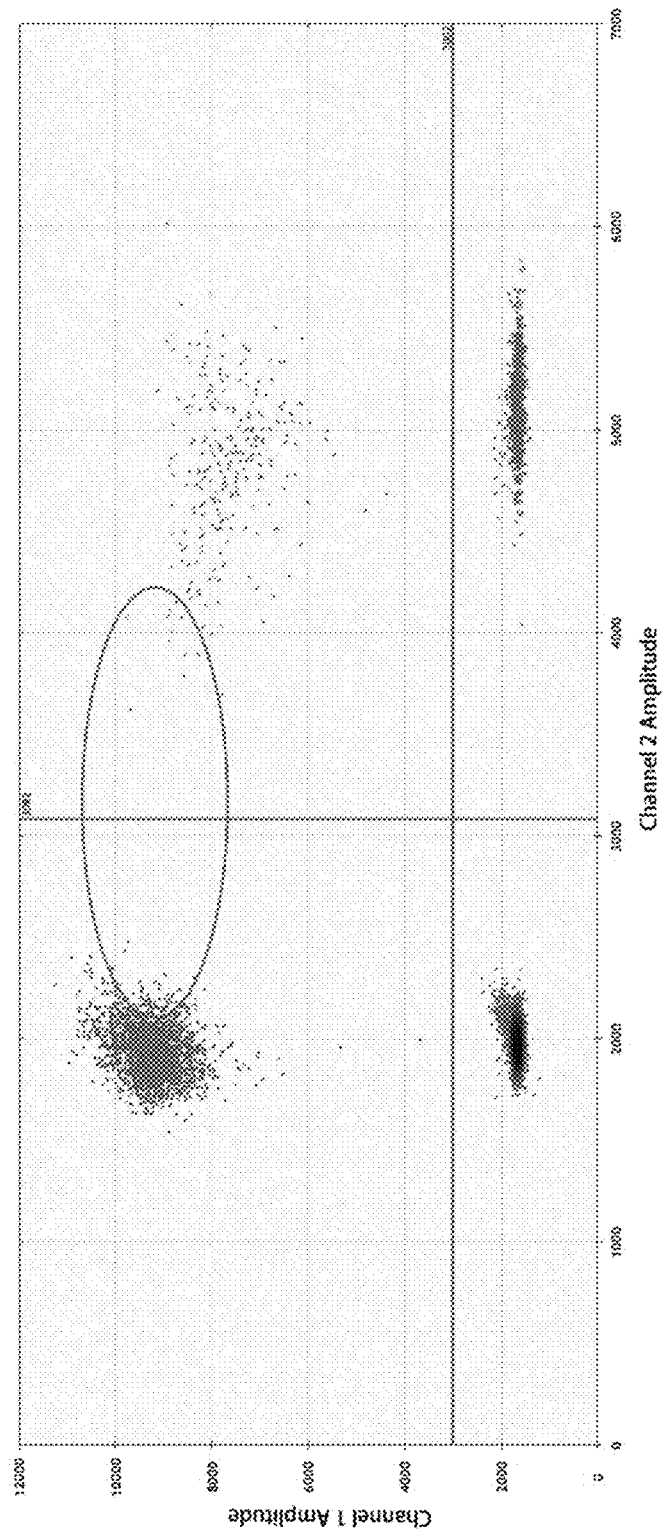

FIG. 8A and FIG. 8B show the detection results of the deletions in exon 19 of EGFR gene (i.e., termed "EGFR exon 19 deletions") using primers and control reagents provided in the present disclosure. FIG. 8A shows a measuring scatter plot for the control reagent, and FIG. 8B shows a measuring scatter plot for the primers.

Figure 9:
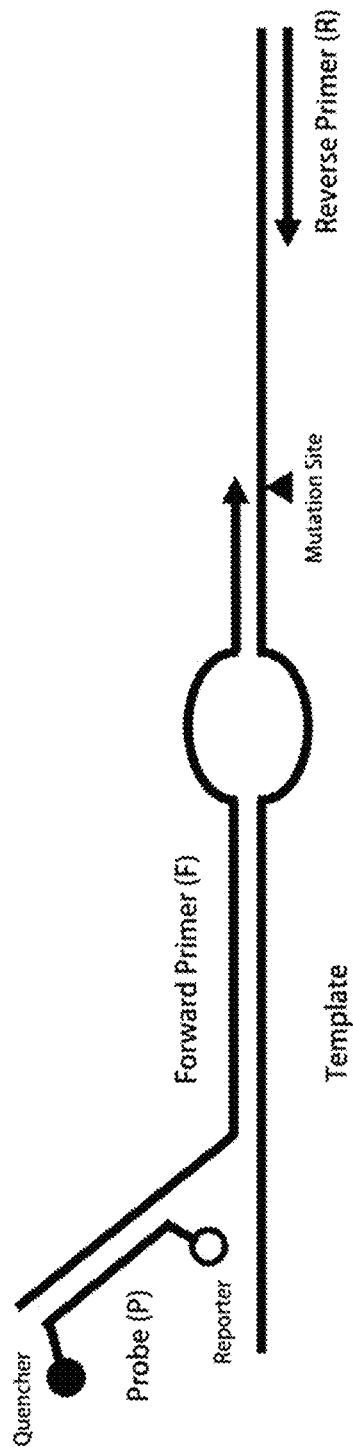

FIG. 9 shows a diagram of a primer design scheme according to some other embodiments of the disclosure.

Figure 10A:
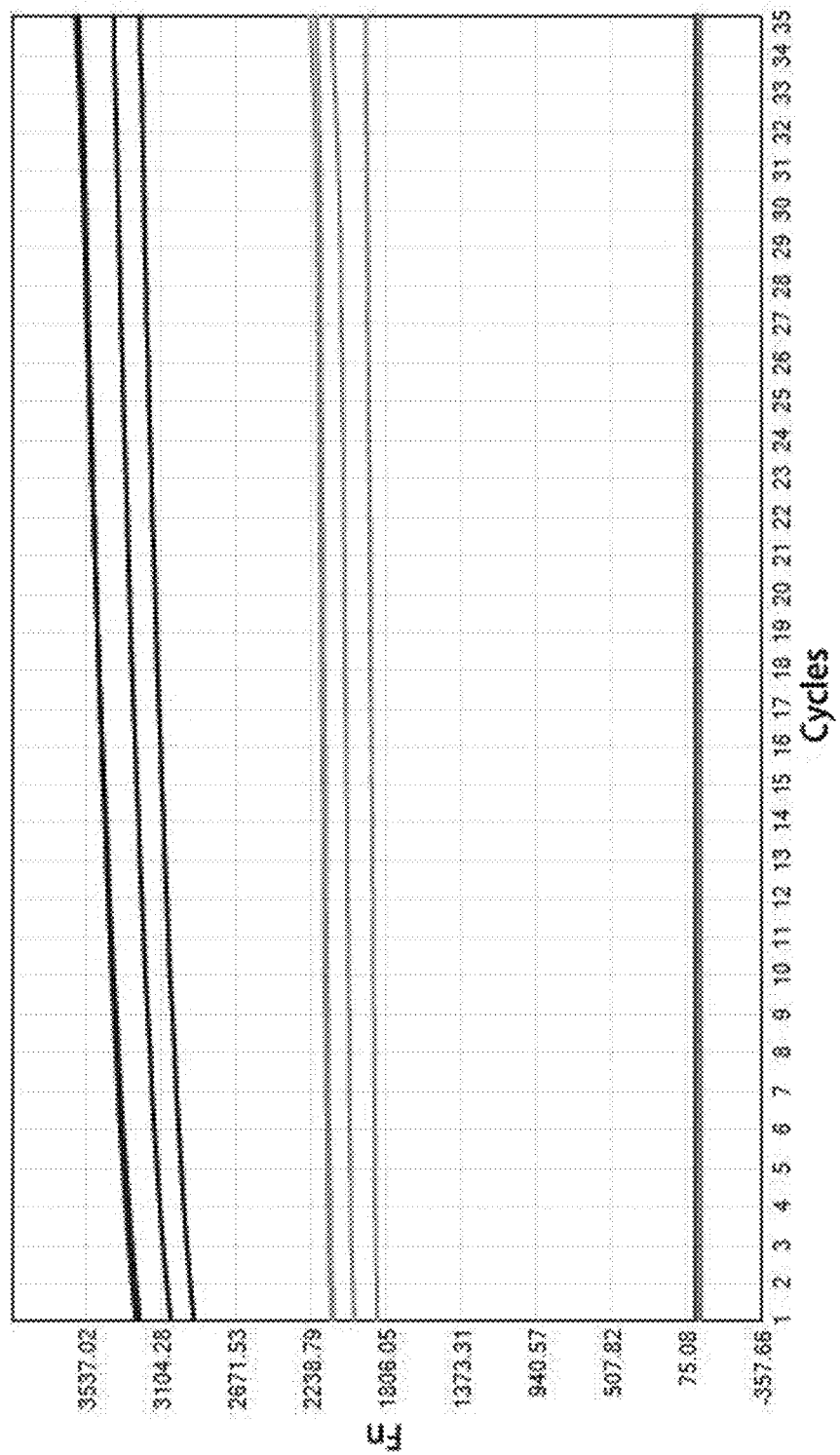
Figure 10B:
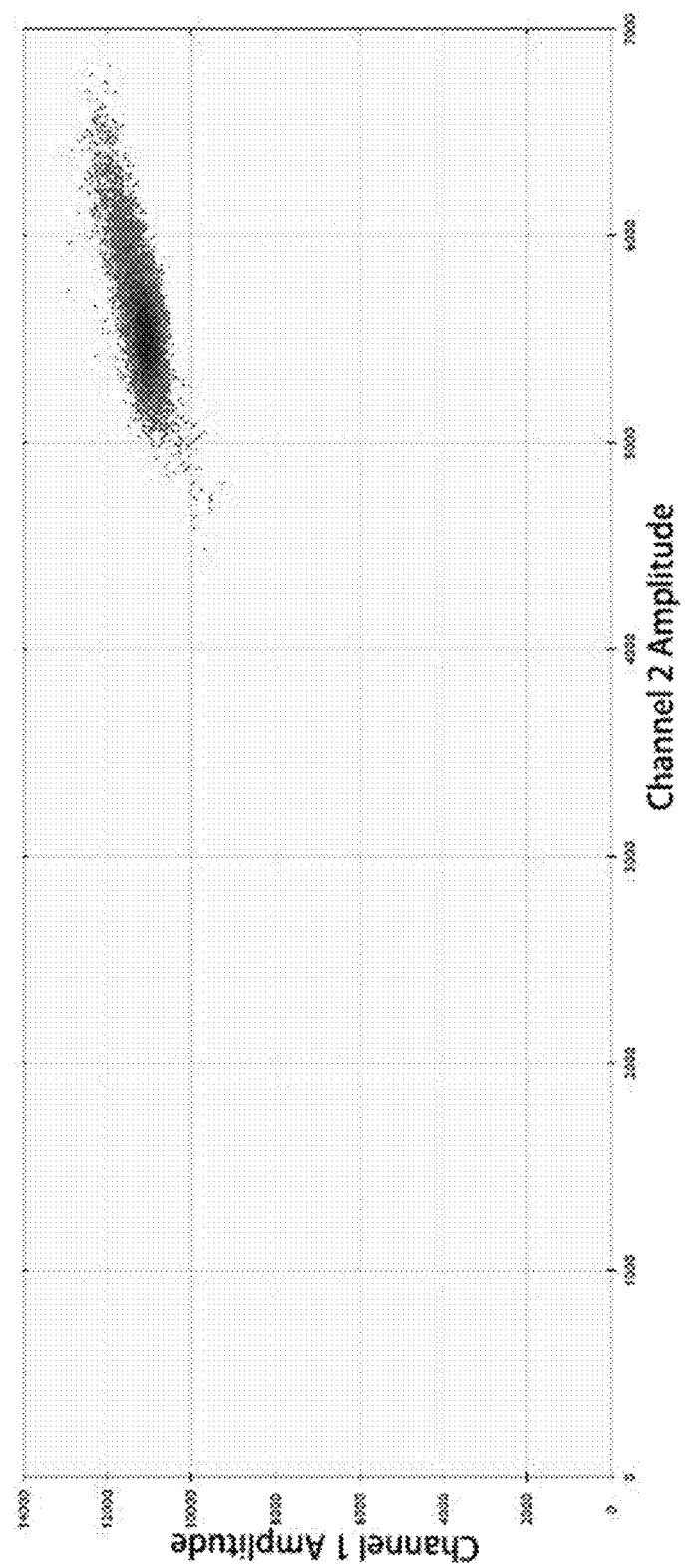

FIG. 10A and FIG. 10B show the detection results of fragmented DNA samples from the Colo 205 cell lines with theoretical mutation abundance of 65.8% by using primers designed based on the scheme shown in FIG. 9. The results of fluorescence quantitative PCR are shown in FIG. 10A and the results of digital PCR are shown in FIG. 10B.

DETAILED DESCRIPTION

Throughout the disclosure, unless otherwise specified, each of the terms disclosed and used herein shall be interpreted to have a meaning that accords to what has been commonly known and used in the art. Therefore, unless otherwise defined, all technical and scientific terms used herein shall be interpreted to have the same meanings as those generally understood by those of ordinary skills in the art. If, however, there is a contradiction between a definition and/or an interpretation provided in this disclosure and a common knowledge, the definition and the interpretation provided in this present disclosure shall dominate.

As used herein, the terms "nucleic acid," "oligonucleotide," and "polynucleotide" are interchangeable, and are used to refer to a single-chain and/or double-chain polymer of nucleotide monomers, which include, but are not limited to, a 2'-deoxyribonucleic acid (DNA) molecule and a ribonucleic acid (RNA) molecule formed through one or more phosphodiester bonds between nucleotides or nucleotide analogues. Each nucleotide monomer in a nucleic acid can be termed as a "nucleotide residue". Each nucleic acid can consist entirely of deoxyribonucleotides, ribonucleotides or their chimeric molecules, and can include one or more nucleotide analogues. A nucleotide monomer may contain any one of the nucleotides described herein, which can include, but is not limited to, a nucleotide and/or nucleotide analogue. Nucleic acids usually vary in size from several nucleotide residues to thousands of nucleotide residues. Among them, an "oligonucleotide" usually referred to a relatively short nucleotide polymer having a size of, for example, 1-80. Unless otherwise indicated, whenever a nucleic acid sequence is presented, it shall be interpreted that the nucleotides are in an order from a 5' end to a 3' end from left to right. Unless otherwise indicated, "A" denotes a deoxyadenosine, "C" denotes a deoxycytidine, "G" denotes a deoxyguanosine, "T" denotes a deoxythymidine, and "U" denotes a deoxyuridine.

Conventionally, a length of a nucleic acid is expressed as a number of bases, a number of base pairs (abbreviated as "bp"), a number of nucleotide/nucleotide residues (abbreviated as "nt") or a count of 1,000 base ("kb"). The terms "bases," "nucleotides," and "nucleotide residue" can describe a single-stranded or a double-stranded polynucleotide, wherever appropriate. In cases where any of the above terms is applied to a double-stranded molecule, it shall be applied to an entire length of the double-stranded molecule, and shall be interpreted as equivalent to the term "base pair".

As used herein, the term "primer" refers to an oligonucleotide that can hybridize with sequences within a target nucleic acid, and can serve as a starting point for synthesis along a complementary chain of the target nucleic acid under a condition suitable for such synthesis.

As used herein, the term "probe" refers to an oligonucleotide that can hybridize with sequences within a target nucleic acid, and is detectably labeled. A probe may contain one or more modifications, such as a 3'-terminal modification and/or a 5'-terminal modification, which enable the probe to be detected or hydrolyzed by a nucleic acid polymerase, etc., and the one or more modifications may also include one or more chromophores.

As used herein, the terms "target sequence", "target nucleic acid" or "target" are interchangeable and are used to refer to a portion of a nucleic acid sequence to be amplified, detected, or amplified and detected, which can be annealed or hybridized with one or more probes or primers under conditions suitable for hybridization, annealing or amplification. The term "hybridization" as used throughout the disclosure is referred to as a base pairing interaction between two nucleic acids, which results in the formation of a double-stranded complex. It is noted that it does not require that the two nucleic acids have 100% complementarity over their full lengths in order to realize a hybridization.

As used herein, the term "forward primer" refers to an oligonucleotide which can anneal or hybridize with a specific strand of a target DNA molecule. Herein the specific strand of the target DNA molecule is usually referred to as an antisense strand.

As used herein, the term "reverse primer" refers to an oligonucleotide which can anneal or hybridize with an opposite strand of the target DNA molecule. Herein the opposite strand of the target DNA molecule is usually referred to as a sense strand.

Those skilled in the art will readily understand that when the designation of a sense strand and an antisense strand switches, the corresponding "forward primer" and "reverse primer" named thereby shall also switch.

As used herein, the terms "upstream," "located at an upstream of," "upstream of," or alike, when used in the context of describing a nucleic acid sequence, refer to a portion/region of the nucleic acid sequence that is closer to a 5'-end thereof relative to a reference portion/reference region in the same nucleic acid sequence. For example, it can be a portion/region immediately adjacent to the reference portion/region, or can be a portion/region having a space of one or more bases from the reference portion/region.

Similarly, the terms "downstream," "located at a downstream of," "downstream of," or alike, when used in the context of describing a nucleic acid sequence, refer to a portion/region of the nucleic acid sequence that is closer to a 3'-end thereof relative to a reference portion/reference region in the same nucleic acid sequence. For example, it can be a portion/region immediately adjacent to the reference portion/region, or can be a portion/region having a space of one or more bases from the reference portion/region.

Unless otherwise specified, when describing a double-stranded nucleic acid, the terms "upstream" and "downstream" are usually defined based on a 5'-end and a 3'-end, respectively, of a sense strand of the double-stranded nucleic acid.

As used herein, the terms "target sequence binding region," "upstream detection region," "amplification determinant site," "mismatch region," "portion (a)" and "portion (b)" refer to different sequence segments located on an F1 primer (i.e., first forward primer). Among them, the "amplification determinant site" and the "mismatch region" are located within the "target sequence binding region", "portion (a)" and "portion (b)" are located within the "upstream detection region".

As used herein, the phrase "target sequence binding region" indicates that this particular region is used for hybridization or annealing with a target sequence, but does not necessarily mean that the region has 100% base complementary pairing with the target sequence, and it possible that there are one or more mismatched regions in the target sequence binding region. A "mutation detection site" is located within a target sequence, and throughout the disclosure, the term "mutation detection site" is referred to as a segment having sequence differences between different target sequences to be detected, such as between a wild-type sequence and a mutant-type sequence. A length of a "mutation detection site" can be one or more base pairs. The mutations that are implicated may be point mutations, deletions, insertions, base inversions, etc., compared with a wild-type target sequence.

As used herein, the terms "TaqMan probe" and "hydrolysis probe" are interchangeable throughout the disclosure. A TaqMan probe is a fluorescence detection technology developed on a real-time PCR platform. A 5' end of a TaqMan probe contains a fluorescence reporter and a 3' end thereof contains a fluorescence quenching group. When a TaqMan probe is complete, the fluorescence signal emitted by the fluorescence reporter is absorbed by the fluorescence quenching group. During the process of PCR amplification, the 5' end to 3'-end exonuclease activity of the Taq DNA polymerase can enzymatically digest the TaqMan probe, which separates the fluorescence reporter from the fluorescence quenching group, thereby emitting out fluorescent signals, so that the accumulation of the fluorescent signals and the formation of the PCR products can be completely synchronized.

Specifically, the fluorescence reporter can comprise FAM, HEX, VIC, ROX, Cy5, Cy3, and other suitable fluorophore known in the art; the fluorescence quenching group can comprise TAMRA, BHQ1, BHQ2, BHQ3, DABCYL, QXL, DDQI, and other suitable quencher(s) known in the ar. It is noted that these above composition examples are for illustrating purposes only and the above recitation shall not be interpreted as limiting the scope of the disclosure.

In addition, TaqMan probes can have other variations (i.e., modified forms). For example, a TaqMan-MGB probe is substantially a TaqMan probe with a minor groove binder (MGB) at a 3-end thereof, which can increase the $T_m$ value of the probe, shorten the length of the probe, and facilitate the simultaneous detection of multiple mutation sites.

As used herein, the abbreviation "F1" and the phrase "first forward primer" are interchangeable, the abbreviation "F2" and the phrase "second forward primer" are interchangeable, the abbreviation "R" and the phrase "reverse primer" are interchangeable, and the abbreviation "P" and "probe" are interchangeable.

As used herein, the term "stringent condition" may encompass any of a low stringent condition, a medium stringent condition, or a high stringent condition. A low stringent condition can be a condition having 5×SSC, 5×Denhardt solution, 0.5% SDS, and 50% formamide, and at 32° C.; a "medium stringent condition" can be a condition having 5×SSC, 5×Denhardt solution, 0.5% SDS, and 50% formamide, and at 42° C.; whereas a "high stringent condition" can be a condition having 5×SSC, 5×Denhardt solution, 0.5% SDS, and 50% formamide, and at 50° C. Under these conditions, the higher the expected temperature, the more effective a polynucleotide (e.g., DNA) can be obtained efficiently. Although there are many factors affecting the stringency of the hybridization, such as temperatures, probe concentrations, probe lengths, ion strengths, time, salt concentrations, etc., similar stringency can be obtained by appropriately selecting these factors.

As used herein, the term "mutation abundance" refers to a relative or absolute quantitative value of a mutant molecule for a target gene. In a detection process, "mutation abundance" is generally defined as a proportion of a number of the mutant molecules for the target gene in a total number of the molecules (e.g., DNA molecules).

As used herein, the term "sample" may represent any composition containing, or presumably containing, nucleic acids. A sample may come from biological sources (i.e., "biological samples"), such as tissues (e.g., biopsy samples), extracts or cultures, and/or biological or physiological fluids. For example, samples may include skin, plasma, serum, spinal cord fluid, lymph, synovial fluid, urine, tears, blood cells, organs, and tumors. In addition, samples may include in vitro cultures from individual cells or immobilized samples, such as formalin-fixed paraffin-embedded tissue (FFPET) and nucleic acid isolates from FFPET.

The inventors of the present disclosure have recognized that, during the process of PCR amplification, there are many factors that may affect the amplification efficiency. There is no guarantee that the amplification efficiency of any particular PCR reaction will remain unchanged throughout the reaction. There is also no guarantee that the amplification efficiencies will remain the same between test samples and standard samples or from samples to samples. As a result, the value of cycle threshold (Ct) typically used as the basis for quantitative analysis is not constant. Therefore, quantitation in qPCR is only "relative quantification" at best. The accuracy and reproducibility of qPCR fall short of the stringent requirements demanded by the quantitative needs of modern molecular biology.

Digital PCR (dPCR) is a technology that allows absolute quantification of nucleic acid molecules. It uses the principle of limiting dilution to distribute a real-time quantitative PCR reaction system to thousands of individual nanoliter microreactors such that each microreactor either contains one or more copies of target nucleic acid molecules (i.e., target DNA sequence) or none. After this dilution, single target template-based PCR amplifications are performed simultaneously in each microreactor. In contrast to conventional real-time quantitative PCR where the fluorescence signals are collected in each amplification cycle, the fluorescence signal of each parallel reaction unit is collected independently after amplification in digital PCR. Using these independently collected signals of each microreactor, the original copy number or the concentration of the target molecule may be determined based on the principle of Poisson distribution and the proportions of positive/negative reaction units.

Compared with conventional real-time quantitative PCR, digital PCR can achieve accurate and absolute quantitative detection of target nucleic acid molecules without relying on Ct values and standard curves. It has the advantages of high sensitivity and accuracy. Because digital PCR only judges the "yes or no" amplification state when interpreting the results, it does not need to detect the intersection points of the fluorescent signals and the pre-set threshold lines, and it does not depend on the identification of Ct value at all. As such, the influence of amplification efficiency variability has on digital PCR reactions is greatly reduced. This independence from amplification efficiency affords digital PCR much more tolerance to the presence of any inhibitor(s) of PCR reaction. In addition, the process of distributing reaction system in performing a digital PCR can greatly reduce the concentrations of any background sequence(s) that can potentially compete with the target sequence, thereby enhancing digital PCR's sensitivity and accuracy, which has obvious advantages over traditional fluorescence quantitative PCR, especially when it comes to quantifying and detecting low-copy differential nucleic acid molecules with high sensitivity. Therefore, digital PCR has great use cases in applications that seek to detect rare variations or mutations in a complex background. Such applications are common in liquid biopsies of tumors (e.g., detection of rare mutation markers in peripheral blood samples of cancer patients), non-invasive prenatal detections, organ transplantation monitoring, accurate quantifications of viral load, detections of components of genetically modified crops, the study of gene expression differences, etc.

At present, many of the existing nucleic acid sequence mutation detection kits use a TaqMan approach involving the use of competitive probes (i.e., "TaqMan probes") or an approach of amplification refractory mutation system (ARMS). The basic principle of the TaqMan probes is to utilize the 5'-exonuclease activity of the Taq enzyme that can cleave an oligonucleotide probe that binds to a target sequence during amplification. The 5'-end of the oligonucleotide probe is labelled with a fluorescence reporter (i.e., fluorescent dye for reporting purposes), and the 3'-end of the oligonucleotide probe is labelled with a fluorescence quencher which is further phosphorylated to prevent probe extension. When primers extend along the template target sequence and reach the binding site of the oligonucleotide probe, the Taq enzyme can cut the oligonucleotide probe into small fragments, which can separate the fluorescence reporter from the fluorescence quencher, thereby allowing the emission of fluorescence. In applications such as differential nucleic acid detections, two competitive probes are commonly utilized: one for a mutant target nucleic acid sequence, and the other for a wild-type target nucleic acid sequence. In practice, however, traditional TaqMan probes often suffer from cross-reaction, especially in situations where the nucleic acid sequence difference is small and difficult for distinguish. In one example where detection of point mutations is desired, there is only one base difference between a wild-type and a mutant type. Cross-reactions of probes can easily affect the specificity of detection reagents to give false negative results or false positive results. In view of the above issues, some detection approaches have utilized a minor groove binder (MGB) to modify competitive probes or utilize locked nucleic acid (LNA) probes to improve the specificity of probes to thereby reduce or avoid cross-reactions. However, these probe modification approaches are commercially difficult to deploy due to their high costs and patent restrictions.

On the other hand, the approach of ARMS takes advantage of the absence of the 3'-exonuclease activity of a DNA polymerase. If the 3' terminal base of a primer does not match the target nucleic acid sequence correctly, the target nucleic acid sequence cannot be amplified effectively. In detection of point mutations, two competitive ARMS forward primers are typically used to amplify the mutant sequence and wild type target nucleic acid sequences.

Because they typically share a common hydrolysis probe and a common reverse primer, it is difficult to detect the mutant sequence and the wild type sequence simultaneously in a single reaction system. Therefore, two separate reaction systems are usually used for the detection of mutant sequence and the wild-type sequence.

In clinical practice, however, application of PCR is often thwarted by the difficulties in obtaining experimental samples, or in obtaining sufficient biological samples from patients in clinical testing. It is especially noted that the concentration of target nucleic acids in peripheral blood samples, urine samples, lavage fluid samples, cerebrospinal fluid samples, and other samples collected during liquid biopsy, is typically very low, and the sensitivity of detection will be greatly reduced and the cost will be greatly increased if separate detection reaction system is to be used, which can greatly limit the clinical applications of the techniques. In addition, common ARMS primers often fail to block non-specific template amplification, and therefor false positive results are easily produced in detection as a consequence. This is especially true in digital PCR systems where the fluorescence signals of the mutant sequence and the wild-type sequence at the end of amplification are often difficult to distinguish, ultimately leads to lack of specificity.

In applying digital PCR technology, mutant and wild-type sequences cannot be distinguished by A Ct because the technique does not depend on the Ct value and the standard curve, but depend only on the intensity of end-point fluorescence signal. Therefore, there is a high requirement for the specificity of primer probes. Cross-reactions must be avoided as much as possible so that any fluorescence signal of the target sequence to be detected can be completely distinguished from that of other background signals or of non-specific signals at the end of amplification. To this end, there still exists a great need for a general primer construct that is capable of delivering high sensitivity, high specificity at low cost to enable more uses cases for digital PCR technology.

Compared with existing technologies, at least some embodiments of the primers, compositions and methods disclosed herein can have one or more of the following advantages:

(1) Requires shorter target nucleic acid sequence: In comparison to conventional primer designs approaches as exemplified by the TaqMan probe approach and the ARMS approach, primer constructs of the present disclosure generally require shorter target nucleic acid fragment with a minimum length of less than 40 bp. This advantage can be reflected in various detection scenarios, such as in the detection of highly fragmented cell-free DNAs. Because DNA fragmentation is random, shorter detection fragments allows for the detection of more DNA targets, thus greatly improving the detection sensitivity.

(2) Has lower requirements for target nucleic acid sequence: Primer probe design disclosed herein can avoid the unbalanced GC region when detecting complex target nucleic acid sequences. At the same time, the approach disclosed herein also makes it less difficult to design specific probe sequences than the TaqMan probe approach and the ARMS approach.

(3) Has higher detection sensitivity: Detection sensitivity of the primers, compositions and methods disclosed herein can reach nearly 0.01% even in a complex background. The kit disclosed herein can stably detect target nucleic acid sequences in a complex background with a sensitivity of 0.05%, which can ensure that ~10 copies of a target nucleic acid sequence can be stably detected (i.e., at a detection rate of >95%) in a background having ~20,000 copies of total nucleic acids, or that ~15 copies of a target nucleic acid sequence can be stably detected in a background having ~30,000 copies of total nucleic acids. As such, the approach disclosed herein can realize a stable detection of low-concentration samples and low-mutation-abundance samples to thereby satisfy a clinical monitoring of cell-free DNA samples from peripheral blood circulation of cancer patients, which is believed to be able to accurately reflect the current state of a patient's disease, to be beneficial in guiding the use of targeted therapies, and in the monitoring of disease prognosis.

(4) Has higher detection specificity: The primers, compositions and methods described in the present disclosure can effectively avoid the occurrence of cross-reactions. In other words, when detecting mutant target nucleic acid sequences, there are no cross-reactions that come from wild-type, or other similar or homologous target nucleic acid sequences. Especially in the simultaneous detection of wild-type and mutant sequences, the cross-reactions between them is relatively small, thereby benefiting the detection of rare mutations.

(5) Has wider scope of application: The approach disclosed herein can be used to detect short-fragment target nucleic acids of less than ~200 bp, and has a relatively good tolerance to PCR inhibitors. It can be applied to the detection of nucleic acids of various sample types, including formalin fixed paraffin-embedded tissue (FFPE) samples, fresh tissue samples, peripheral blood samples, urine samples and lavage fluid samples, cerebrospinal fluid samples, cultured cell lines, and synthetic plasmid samples, etc.

(6) Has lower sample consumption rate: The approach disclosed herein can simultaneously detect mutant and wild-type target nucleic acid sequences in a reaction system or a reaction unit, and can be used to absolutely quantify and count mutant abundance of the mutant and wild-type target nucleic acid sequences. It has significant advantages over the existing technologies especially when used in working with rare samples, such as DNA detection of circulating tumors in peripheral blood samples.

(7) Has lower cost: The primers and its reaction system components of the present disclosure do not need to undergo expensive MGB or LNA modification, which can greatly reduce the cost of manufacturing primer probes, while still ensuring a better detection performance.

EXAMPLES

In the following, with reference to the various specific embodiments described in detail, the advantages and effects of the technical solutions provided herein will be presented in a clear fully understandable manner. It should be noted that the embodiments that are described represent merely a portion but not all of the embodiments of the disclosure. Based on the described embodiments of the disclosure, those ordinarily skilled in the art can obtain other embodiment(s), which come(s) within the scope sought for protection by the disclosure.

| Materials and Equipment | |
| --- | --- |
| Equipment/Materials | Manufacturer/Model |
| 2X ddPCR Supermix for Probes | Bio-Rad, #1863010 |
| DG8 Cartridges for QX200 Droplet Generator | Bio-Rad, #1864008 |

-continued

| Materials and Equipment | |
|---|---|
| Equipment/Materials | Manufacturer/Model |
| DG8 Droplet Generation Oil for probes | Bio-Rad, #1863005 |
| DG8 gasket for ddPCR | Bio-Rad, #1863009 |
| ddPCR Droplet Reader Oil | Bio-Rad, #1863004 |
| Droplet Digital PCR Plates, 96-well, semi-skirted | Eppendorf, #30128575 |
| QX200 Droplet Generator | Bio-Rad, #1864002 |
| PX1 PCR Plate Sealer | Bio-Rad, #1814000 |
| PCR Thermal Cycler | Bio-Rad, #1851197 |
| QX200 Droplet Reader | Bio-Rad, #1864003 |
| Colo 205 cell line | Cobioer, #CBP-60026 |
| primers | synthesized by Sangon Biotech |
| probes | synthesized by Sangon Biotech |
| nucleic acid fragmentase (KAPA Frag Kit) | Roche, #7962495001 |
| analysis software | Bio-Rad, QuantaSoft digital PCR analysis software |

Example 1

In this example, the general purpose is to select a common nucleic acid mutation as an example to test the primer and detection system provided in the disclosure. Specifically, the V600E mutation of human BRAF gene (short as "BRAF V600E mutation" hereinafter) is used as an example to simulate clinical samples to evaluate the performance of the detection system disclosed herein.

BRAF gene mutation is found in about 8% of human tumors. BRAF mutation can drive the proliferation, growth and differentiation of tumors, especially in colorectal cancer (5%-8%), thyroid cancer (5%-20%) and melanoma (40%-68%). Different proportions of BRAF mutation are also found in lung cancer, liver cancer and pancreatic cancer. About 89% of the mutations occur in the activation region of exon 15 in the BRAF gene. Most of the mutations occur at the base "T" at position 1799 of the nucleotide sequence in BRAF and result in an amino acid substitution of a valine residue at position 600 by a glutamate residue (V600E).

Detection of such a point mutation or alike is generally directed to circulating tumor DNA (ctDNA) in a patient's peripheral blood, which can be used for early screening, guidance of medication, prognosis and recurrence monitoring of cancer patients. However, due to the complex background of peripheral blood samples and the scarcity of the ctDNA content, conventional approaches including fluorescence quantitative PCR, molecular hybridization, capillary electrophoresis, and second-generation sequencing, etc. are vulnerable to the background interference; they are incapable of delivering the level of sensitivity and accuracy required for clinical diagnostic use. Conventional digital PCR approaches also not able to overcome the background interference issue and typically require exotic modifications to the probes such as LNAs or MGB modifications, thereby resulting in a significantly increased detection cost.

As demonstrated below, primer construct disclosed in the present disclosure does not suffer from the above-mentioned shortcomings. They do not require un-natural modifications, yet still deliver high levels of sensitivity, specificity, and accuracy at relatively low cost.

1. Sample Preparation

Fragmented DNA samples from the Colo 205 cell line, which contain the BRAF V600E mutation with a theoretical mutation abundance of 65.8% and independently validated by digital PCR, were used to simulate clinical circulating tumor DNA (ctDNA) samples.

Specifically, genomic DNA of the Colo 205 cell line containing the BRAF V600E mutation was extracted by QIAGEN QIAamp® DNA Mini Kit according to the instructions of the kit, to thereby obtain the genomic DNA from the cell line containing the BRAF V600E mutation. Then a KAPA Frag Kit was used to enzymatically fragment the genome DNA extracted from the cell line containing the BRAF V600E mutation, to thereby obtain a fragmented mutant DNA with a length of ~120-130 bp, which can thus simulate DNA fragments in a clinical circulating tumor DNA (ctDNA) sample.

Similarly, genomic DNA from healthy individuals was also prepared and confirmed to contain no BRAF V600E mutation using next generation sequencing (NGS). The genomic DNA also underwent enzymatic fragmentation to thereby obtain a fragmented wild-type DNA sample to simulate a clinical cell-free DNA sample.

The fragmented mutant DNA sample and the fragmented wild-type DNA sample were mixed in certain ratios, and such mixed DNA sample was then quantified by digital PCR. The fragmented mutant DNA sample was then diluted by the fragmented wild-type DNA sample to thereby obtain a series of diluted samples with theoretical mutation abundance of 5%, 1%, 0.5%, 0.2%, 0.1% and 0.05%, respectively. The total DNA concentration in each of these above diluted DNA samples was 20,000 copies/μL. The fragmented wild-type DNA sample and the fragmented mutant DNA sample, each having a same concentration of total DNA (20,000 copies/μL), were respectively used as a negative control and a positive control. A DNA-free Tris-EDTA buffer was used as a blank control.

2. Reaction System Preparation 2.1 Primers and Probes

The primers and probes were synthesized from Sangon Biotech Co. Ltd.

The sequences for the primers and the probes are as follows:

The sequence of the mutant F1 primer is set forth in SEQ ID NO: 1; the sequence for the wild-type F1 primer is set forth in SEQ ID NO: 2; the sequence for the mutant F2 is set forth in SEQ ID NO: 3; the sequence for the wild-type F2 is set forth in SEQ ID NO: 4; the sequence for the mutant probe P is set forth in SEQ ID NO: 5, the sequence for the wild-type probe P is set forth in SEQ ID NO: 6, the sequence for the reverse primer R is set forth in SEQ ID NO: 7.

The mutant probe P (i.e., SEQ ID NO: 5) is labelled with an FAM at its 5' end and a BHQ1 at its 3' end. The wild-type probe P (i.e., SEQ ID NO: 6) is labelled with a HEX at its 5' end and a BHQ1 at its 3' end.

The mutant F1 primer (i.e., SEQ ID NO: 1) has a full length of 62 bp, and the wild-type F1 primer (i.e., SEQ ID NO: 2) has a full length of 61 bp. The first 23 bases segment from the 3'-end of each of these above two primers corresponds to a target sequence binding region. The last base at the 3' end corresponds to the BRAF V600E mutation site, and the third base at the 3'-end introduces a mismatch base to enhance the amplification blockade.

TABLE 1

| Primers/Probes | | SEQ ID NO | Nucleotide sequence (from 5' end to 3' end) | Modification |
|---|---|---|---|---|
| BRAF V600E mutation Detection | mutant F1 | SEQ ID NO: 1 | ACCGACAGTGGTACGCAACGATTCCTATGCTCGCTGTCGGGTGATTTTGGTCTAGCTACTGA | none |
| | wild-type F1 | SEQ ID NO: 2 | GCGTCACGTCCTGAAGCAGTCGTTTCGCAGATCGCTCGGGTGATTTTGGTCTAGCTACGGT | none |
| | mutant F2 | SEQ ID NO: 3 | ACCGACAGTGGTACGC | none |
| | wild-type F2 | SEQ ID NO: 4 | GCGTCACGTCCTGAAG | none |
| | mutant probe P | SEQ ID NO: 5 | ACGATTCCTATGCTCGCTGT | 5'FAM 3'BHQ1 |
| | wild-type probe P | SEQ ID NO: 6 | AGTCGTTTCGCAGATCGCT | 5'HEX 3'BHQ1 |
| | reverse primer R | SEQ ID NO: 7 | CCTCAATTCTTACCATCCACAA | none |

The first 16 bases segment at the 5' end of each of the mutant F1 primer and the wild-type F1 primer corresponds to the portion (a) of the upstream detection region, which are identical to the base sequences of a corresponding F2 primer (i.e., the mutant F2 primer, set forth in SEQ ID NO: 3, and the wild-type F2 primer, set forth in SEQ ID NO: 4, respectively).

A segment of the mutant F1 primer from the 18th base to the 37th base from the 5' end thereof corresponds to the portion (b) of the upstream detection region, and the sequence of the segment is the same as that of the corresponding mutant probe P (SEQ ID NO: 5).

A segment of the wild-type F1 primer from the 18th base to the 36th bases from the 5' end thereof corresponds to the portion (b) of the upstream detection region, and the sequence of the segment is the same as that of the corresponding wild type probe P (SEQ ID NO: 6).

Therefore, after specific amplification of a target nucleic acid using the mutant F1 primer and the wild-type F1 primer, the amplified product is added with a sequence from the 5' end of the corresponding F1 primer and its complementary sequence. Then a corresponding F2 primer and a corresponding probe P can hybridize with the corresponding target nucleic acid template and emit fluorescent signals after hydrolysis.

2.2 Reaction System

A PCR reaction mixture was prepared according to the following recipe (in a 20 μL reaction system).

TABLE 2

| | Reagents | Concentration in final reaction |
|---|---|---|
| BRAF V600E mutation Detection | 2X ddPCR ™ Supermix for Probes | Dilted to 1X in final reaction |
| | mutant F1 | 45 nM |
| | wild-type F1 | 45 nM |
| | mutant F2 | 450 nM |
| | wild-type F2 | 450 nM |
| | mutant probe P | 250 nM |
| | wild-type probe P | 250 nM |
| | reverse primer R | 900 nM |
| | DNA sample | 0.05-3 ng/μL |
| | ddH$_2$O | Til 20 μL |

2.3 Preparation of Reaction Unit

A PCR reaction of 20 μL prepared in the above table was added to a sample well in a microdroplet occurrence card. Then 70 μL of microdroplet generation oil was added to an oil well in the microdroplet occurrence card. Finally, the microdroplet generation cartridge was sealed with a gasket.

The microdroplet generation cartridge prepared above was then placed into a droplet generator for droplet generation. After about 2 minutes of droplet generation, and the microdroplet generation cartridge was then dismounted, and a droplet suspension of about 40 μL was transferred from a top row of wells to a well in a 96-well PCR plate.

3. Amplification and Signal Reading

After sealing the 96-well PCR plate, it placed in a PCR thermal cycler for PCR amplification. The PCR procedures is as follows: pre-denaturation at 95° C. for 10 minutes; denaturation at 94° C. for 30 seconds and annealing at 65° C. for 60 seconds, for five cycles; denaturation at 94° C. for 30 seconds and annealing at 55° C. for 60 seconds, for 40 cycles; inactivation at 98° C.; and terminating the PCR reaction at 10° C.

At the end of the PCR amplification, the 96-well plates were placed in a microdroplet analyzer, and the FAM/HEX channel was selected for signal reading.

4. Statistics and Analysis

The QuantaSoft analysis software was used to analyze the intensity and number of fluorescent signals to thereby obtain the copy number and the concentration of the BRAF V600E mutant and the copy number and the concentration of the BRAF V600 wild type.

Based on the presence or absence of fluorescence signal, the proportion of negative/positive microdroplets can be determined, and the concentrations of the mutant sample and the wild-type sample can be obtained, and then the mutant abundance of target nucleic acid sequence in the sample can be calculated through the following formula:

[[mutant concentration]/(mutant concentration+wild type concentration)]*100%

For example, the target nucleic acid concentration of BRAF V600E mutant was 50 copies/μL in the sample to be tested, and the target nucleic acid concentration of BRAF V600 wild type was 9950 copies/μL. The abundance of BRAF V600E mutant in the sample to be tested was as follows:

[(50 copies/μL)/(50 copies/μL+9950 copies/μL)]*100%=0.5%

The detection results of the negative control samples using the kit provided in this disclosure are shown in FIG. 2, and the detection results of the positive control samples with a theoretical dilution of 0.1% using the kit provided in this disclosure are shown in FIG. 3.

Using the kit provided in this disclosure, and based on the calculation method recommended by Clinical and Laboratory Standards Institute (CLSI), i.e., the CLSI EP17-2 file, a total of 21 repeated tests were performed over the negative control samples. The Limit of Blank (LoB) of the kit is 0.016%, that is, the sample with mutation abundance of greater than 0.016% will be determined as positive.

Using the kit provided in this disclosure, and based on the calculation method in the CLSI EP17-2 file, a total of 21 repeated tests were carried out on a low-value sample (i.e., diluted sample with theoretical mutation abundance of 0.05%). The Limit of Detection (LoD) of the kit was determined to be 0.038%, which was calculated through the formula:

$$LoD = LoB + DS\beta.$$

Using the kit provided in this disclosure, a total of 21 repeated tests were carried out on the diluted samples with theoretical mutation abundance of 0.1%, 0.2%, 0.5%, respectively. The lowest mutation abundance of CV<20% is determined to be 0.2%. In other words, the kit can have an acceptable quantitative precision and accuracy for a sample having a mutation abundance of >=0.2%. Therefore, the Limit of Quantification (LoQ) of the kit is 0.2%.

The above-mentioned "Limit of Blank" is defined as the highest possible measurement result when measuring blank samples at a certain probability (generally 95%). The above-mentioned "Limit of Detection" is defined as the lowest concentration of the detected substance that can be detected by the detection method. The above-mentioned "Limit of Quantification" is defined as the measurement that the detection method can obtain reliable results, where the quantitative precision and accuracy are acceptable under a specified experimental condition.

Using the kit disclosed herein, a series of diluted samples (5%, 1%, 0.5%, 0.2%, 0.1%, 0.05%) were tested, and each sample underwent three times of repeated test using the kit. A linear correlation coefficient $R^2$ for the kit was determined to be of more than 0.99.

Using the kit disclosed herein, through 21 independent repeated tests on the diluted samples with theoretical mutation abundance of 0.2% and 0.5%, respectively, the measurement precision of the kit was determined. For a diluted sample with theoretical mutation abundance of 0.2%, the CV value of the quantitative results is 16.22%. For a diluted sample with theoretical mutation abundance of 0.5%, the CV value of the quantitative results is 13.02%. Both of these above CV values are less than 20%.

Using the kit disclosed herein, the negative coincidence rate of the test results of negative controls and blank controls is 100%, and the positive coincidence rate of the test results of diluted samples with theoretical mutation abundance down to about 0.05% is 100%.

Based on the above verification experiments, the minimum detection limit of the kit can be as low as 0.038% in terms of the mutation abundance, while in comparison, the sensitivity of existing digital PCR reagents is generally above 0.1% in terms of the mutation abundance, and the sensitivity of existing real-time quantitative PCR reagents is generally only 1% in terms of the mutation abundance. As such, the sensitivity of the kit disclosed herein is much higher than that of existing gene mutation detection kits in the market.

Based on the above verification experiments, the quantitative limit of the kit can be as low as 0.2% in terms of the mutation abundance, and the linear range of mutation abundance between 5% and 0.05% can still keep $R^2$ of >0.99.

Existing gene mutation detection kits can only be used for qualitative analysis, but cannot be used for quantitative analysis of mutation abundance of specific mutations. Even for similar products under development, the quantitative limit is usually higher than 1% in terms of the mutation abundance. Therefore, the quantitative precision and accuracy of the kit are much higher than those of similar or existing gene mutation detection kits.

Example 2

In this example, the DNA sample from the Colo 205 cell line (containing the BRAF V600E mutation) was used to compare with existing gene mutation detection kits.

1. Sample Preparation

The sample preparation is substantially same as Example 1, except that fragmented DNA samples with a mutation abundance of 65.8%, which were obtained from the Colo 205 cell line (having BRAF V600E mutation), were used, and that no series of dilution and preparation of samples were carried out.

2. Reaction System

Preparation of the primer system disclosed in this example is similar to that in Example 1 as described above.

The "PrimePCR™ ddPCR Mutation Assay Kit: BRAF WT for P. V600E, and BRAF P. V600E" kit (#1863100) from Bio-Rad was used as a comparative kit, and the process was carried out based on the manufacturer's instructions. The reaction preparation was shown in Table 3.

TABLE 3

| | Reagents | Concentration in final reaction |
|---|---|---|
| BRAF V600E mutation Detection | 2X ddPCR™ Supermix for Probes | 1X |
| | PrimePCR™ ddPCR Mutation Assay Kit: BRAF WT for p.V600E | 1X |
| | PrimePCR™ ddPCR Mutation Assay Kit: BRAF p.V600E | 1X |
| | DNA sample | 0.005-3 ng/μL |
| | ddH$_2$O | Til 20 μL |

3. Preparation f Reaction Unit

A PCR reaction of 20 μL prepared in the above table was added to a sample hole in a microdroplet occurrence card. Then 70 μL of microdroplet occurrence oil was added to an oil hole in the microdroplet occurrence card. Finally, the microdroplet occurrence card was sealed with a sealing strip.

The microdroplet occurrence card prepared above was then disposed into a droplet generator for the generation of microdroplets. About 2 minutes later, the preparation of the microdroplets was completed, and the microdroplet occurrence card was then dismounted, and a microdroplet suspension of about 40 μL was transferred from a top row of holes to a well of a 96-well PCR plate.

4. Amplification and Signal Reading

After sealing the 96-well PCR plates, they were placed in a PCR thermal cycler for PCR amplification. The PCR procedures is as follows: pre-denaturation at 95° C. for 10 minutes; denaturation at 94° C. for 30 seconds and annealing at 65° C. for 60 seconds, for five cycles; denaturation at 94° C. for 30 seconds and annealing at 55° C. for 60 seconds, for 40 cycles; inactivation at 98° C.; and terminating the PCR reaction at 10° C.

Bio-Rad's comparative kit uses the following procedures: pre-denaturation at 95° C. for 10 minutes; denaturation at 94° C. for 30 seconds and annealing at 55° C. for 60 seconds, for a total of 40 cycles; inactivation at 98° C. for 10 minutes; and terminating the PCR reaction at 10° C.

At the end of the PCR amplification, the 96-well plates were placed in a microdroplet analyzer, and the FAM/HEX channel was selected for signal reading.

5. Statistics and Analysis

The QuantaSoft analysis software was used to analyze the intensity and number of fluorescent signals to thereby obtain the copy number and the concentration of the BRAF V600E mutant and the copy number and the concentration of the BRAF V600 wild type, based on which the mutant abundance was further calculated.

The detection results over the fragmented DNA samples from the Colo 205 cell line using the kit provided herein and the primer system are shown in FIG. 4A, and those of the same sample using the comparative kit from Bio-Rad are shown in FIG. 4B. Both figures are 2-D scatter plots, in which the lower left quadrant represents "double negative" microdroplets (i.e., containing neither a wild-type target nucleic acid template nor a mutant target nucleic acid template); the upper left quadrant represents "mutant positive" microdroplets (i.e., containing only mutant target nucleic acid template and no wild-type target nucleic acid template); the lower right quadrant represents "wild-type positive" microdroplets (i.e., containing only wild-type target nucleic acid template and no mutant target nucleic acid template); and the upper right quadrant represents "double positive" microdroplets (i.e., containing both wild-type and mutant target nucleic acid templates).

Because there is only one base difference between the wild-type nucleic acid template and the mutant target nucleic acid template, the wild-type and mutant signals in "double positive" microdroplets are easy to cross-interfere, resulting in inaccurate threshold division. As can be seen from the comparison between FIG. 4A and FIG. 4B, the kit provided in this disclosure is less likely to cause cross-interference in the detection of "double positive" microdroplets, thus making the threshold division more accurate, resulting in a relatively higher detection accuracy for very low concentration target nucleic acids.

The mutation abundance of the fragmented DNA sample obtained from the Colo 205 cell line that was detected and quantified by the kit provided in the disclosure is 65.8%, and the mutation abundance of the same sample that was detected and quantified by the Bio-Rad comparative kit is 65.7%. There is no significant difference between the two detection results.

The use of the kit disclosed herein does not require modification of the probes, so that the detection cost can be greatly reduced. The cost for the primers and the probes is only about one percent of the cost of the primers and probes in the Bio-Rad comparative kit.

Example 3

In this example, the detection results using F1 primers with longer mismatch regions were tested. The specific steps are as follows:

1. Sample Preparation:

The sample preparation is substantially same as in Example 1.

2. Reaction System Preparation 2.1 Primers and Probes

The primers and probes were synthesized from Sangon Biotech, Ltd.

The sequences for the primers and the probes are as follows:

TABLE 4

| Primers/Probes | SEQ ID NO | Nucleotide sequence (from 5' end to 3' end) | Modification |
| --- | --- | --- | --- |
| BRAF V600E mutation Detection 2 | mutant F1 SEQ ID NO: 8 | ACCGACAGTGGTACGCAACGATT CCTATGCTCGCTGTCGCCTCACA GTAAAAATAGGAATCATCAACAT CTCTACAGA | none |
| | wild-type F1 SEQ ID NO: 9 | GCGTCACGTCCTGAAGCAGTCGT TTCGCAGATCGCTCGCCTCACAG TAAAAATAGGTATCCATAATACT CCTACAGT | none |

The sequences for the primers and the probes used in this example are as follows: the mutant F1 primer (SEQ ID NO: 8); the wild-type F1 primer (SEQ ID NO: 9); the mutant F2 primer (SEQ ID NO: 3); the wild-type F2 primer (SEQ ID NO: 4); the mutant probe P (SEQ ID NO: 5), the wild-type probe P (SEQ ID NO: 6), the reverse primer R (SEQ ID NO: 7).

The mutant F1 primer (i.e., SEQ ID NO: 8) has a full length of 78 bp, and the wild-type F1 primer (i.e., SEQ ID NO: 9) has a full length of 77 bp. The first 39 bases segment from the 3'-end of each of these above two primers corresponds to a target sequence binding region. The last base at the 3' end corresponds to the BRAF V600E mutation site. A 14 base-segment from the $8^{th}$ base to the $21^{st}$ base counting from the 3'-end of each of these above two primers corresponds to a mismatch region to enhance the amplification blockade. The portions introduced at the 5' end of each of the F1 primers (i.e., the mutant F1 primer and the wild-type F1 primer), including the portions having sequences respectively corresponding to the F2 primer and the probe P, are substantially same as the Example 1.

2.2 Reaction System:

The PCR reaction system disclosed in this example is substantially same as that in Example 1 as described above.

2.3 Preparation of Reaction Unit

A PCR reaction of 20 μL prepared in the above table was added to a sample hole in a microdroplet occurrence card. Then 70 μL of microdroplet occurrence oil was added to an oil hole in the microdroplet occurrence card. Finally, the microdroplet occurrence card was sealed with a sealing strip.

The microdroplet occurrence card prepared above was then disposed into a droplet generator for the generation of microdroplets. About 2 minutes later, the preparation of the microdroplets was completed, and the microdroplet occurrence card was then dismounted, and a microdroplet suspension of about 40 μL was transferred from a top row of holes to a well of a 96-well PCR plate.

3. Amplification and Signal Reading

After sealing the 96-well PCR plates, they were placed in a PCR thermal cycler for PCR amplification. The PCR procedures is as follows: pre-denaturation at 95° C. for 10 minutes; denaturation at 94° C. for 30 seconds and annealing at 65° C. for 60 seconds, for five cycles; denaturation at 94° C. for 30 seconds and annealing at 55° C. for 60 seconds, for 40 cycles; inactivation at 98° C.; and terminating the PCR reaction at 10° C.

At the end of the PCR amplification, the 96-well plates were placed in a microdroplet analyzer, and the FAM/HEX channel was selected for signal reading.

4. Statistics and Analysis

The QuantaSoft analysis software was used to analyze the intensity and number of fluorescent signals to thereby obtain the copy number and the concentration of the BRAF V600E mutant and the copy number and the concentration of the BRAF V600 wild type, based on which the mutant abundance was further calculated.

The detection results of the negative control sample by the kit provided in this disclosure are shown in FIG. 5A, and the detection result of the fragmented DNA sample from the Colo 205 cell line with theoretical dilution of 65.8% is shown in FIG. 5B. As shown in the figures, the detection results of the BRAF V600E mutation using the primers described in the present example is substantially same as that of the primers described in the Example 1 and in the Example 2.

Example 4

In order to further verify the effect of the primers and methods provided in the disclosure, a second gene mutation (i.e., L858R mutation of human EGFR gene, short as "EGFR L858R mutation" hereafter) was detected in this example. EFGR is a common driver gene in non-small cell lung cancer. Its mutation mainly occurs in exons 18/19/20/21, and notably over 45% of EGFR-driven mutations are caused by the substitution of an amino acid residue at position 858, encoded in exon 21, from leucine (L) to arginine (R). The above mutations cause the continuous activation of downstream pathway of EGFR, leading to the occurrences of tumors. At the same time, in the process of targeted therapy, tumors caused by the EGFR L858R mutation have been found to be sensitive to the first-generation EGFR tyrosine kinase inhibitors (EGFR-TKI). Therefore, quantitative detection and continuous tracking of the EGFR L858R mutation are particularly important for targeted therapy.

In this specific example, three different primer amplification systems were set up, and the lengths of the amplifier and the template detection ability of the primers were explored.

Similarly, genomic DNA from healthy subjects was also prepared. After the second-generation sequencing confirmed that there was no EGFR L858R mutation, the genomic DNA also underwent enzymatic fragmentation to thereby obtain a fragmented wild-type DNA sample to simulate a clinical cell-free DNA sample.

The fragmented mutant DNA sample and the fragmented wild-type DNA sample were quantified using digital PCR. The fragmented mutant DNA sample was then diluted by the fragmented wild-type DNA sample to thereby obtain a series of diluted samples with theoretical mutation abundance of 12%. The total DNA concentration in the above diluted DNA sample was 20,000 copies/μL.

2. Reaction System Preparation 2.1 Primers and Probes

Three parallel amplification detection systems were set up in this embodiment, and the sequences for the primers and the probes are as follows:

System 1: the specific sequences for the primers and probes used in this system are detailed in Table 5.

TABLE 5

| Primers/Probes | | SEQ ID NO | Nucleotide sequence (from 5' end to 3' end) | Modification |
|---|---|---|---|---|
| EGFR L858R mutation Detection System 1 | mutant F1 | SEQ ID NO: 10 | TACCGACAGTGGTACGCAACGAT TCCTATGCTCGCTGTCGGTCAAG ATCACAGATTTTGGACTAGTCCG | None |
| | wild-type F1 | SEQ ID NO: 11 | CACAGTCGTGCCTCCATCATCGC ACCTACCGCAGACTCGCATGTCA AGATCACAGATTACATGTCTGGG CT | None |
| | mutant F2 | SEQ ID NO: 12 | ACCGACAGTGGTACGC | None |
| | wild-type F2 | SEQ ID NO: 13 | CACAGTCGTGCCTCCATCA | None |
| | mutant probe P | SEQ ID NO: 14 | ACGATTCCTATGCTCGCTGT | 5'FAM 3'BHQ1 |
| | wild-type prope P | SEQ ID NO: 15 | CGCACCTACCGCAGACTCG | 5'HEX 3'BHQ1 |
| | reverse primer R | SEQ ID NO: 16 | ATGGTATTCTTTCTCTTCCG | None |

Two different F1 primers were used to amplify mutant and wild-type target nucleic acid sequences respectively. The mutant F1 primer (SEQ ID NO: 10) includes a segment of 7 mismatched bases at a region positionally corresponding to the $3^{rd}$ to the $9^{th}$ bases near the 3' end thereof to enhance the blocking effect so as to further enhance the specificity of the primer. The wild-type F1 primer (SEQ ID NO: 11) includes a segment of 7 mismatched bases at a region positionally corresponding to the $7^{th}$ to $13^{th}$ bases near the 3' end thereof to enhance the blocking effect so as to further enhance the specificity of primer. At the same time, the two F2 primers and the two probes P do not bind to the F1 primers corresponding thereto, nor do they bind to any target sequences. Only after specific pre-amplification of the target nucleic acid sequences by the F1 primers, the F2 primers and the probes P can bind to the products after pre-amplification, which then allow the hydrolysis of the probes P. The hydrolysis reaction further allows the report groups to be separated from the quenchers, thereby releasing detectable signals.

System 2: The "PrimePCR™ ddPCR Mutation Assay Kit: EGFR WT for p.L858R, and EGFR p.L858R" (#1863104) from Bio-Rad was used according to the manufacturer's instructions.

System 3: substantially same to system 1, except that a different reverse primer R (SEQ ID NO: 17, see Table 6) was used. Thus, the amplicon obtained herein has a different length compared with that in system 1.

TABLE 6

| Primers/Probes | SEQ ID NO | Nucleotide sequence (from 5' end to 3' end) | Modification |
|---|---|---|---|
| EGFR L858R mutation Detection System 3 | reverse primer R | SEQ ID NO: 17 | CTCCTTACTTTGCCTCCTTC | none |

Typically, the cell-free DNAs and circulating tumor DNAs in plasma are highly fragmented, where the average length of the cell-free DNA is about 160 bp, and the average length of circulating tumor DNAs is about 130 bp. As such, the shorter the length of the amplicons in a detection system, the higher the detection rate of the templates. The amplicon length and theoretical template detection rate in each reaction system were determined as follows.

TABLE 7

|  | Amplicon Length | Theoretical template detection rate | Formula used |
|---|---|---|---|
| Detection System 1 | 60 | 53.8% | theoretical template detection rate = (130-amplicon length)/130 |
| Detection System 2 | 73 | 43.8% |  |
| Detection System 3 | 83 | 36.2% |  |

In each reaction system, a total of 4 repeated tests were performed on the diluted samples having theoretical mutation abundance of 12%.

2.2 Reaction System:

The PCR reaction system in system 1 and system 3 as disclosed herein is substantially same as that in Example 1 as described above. The PCR reaction system in system 2 as disclosed herein is substantially same as that of the Bio-Rad comparative kit in Example 2 as described above, except that the kit "PrimePCR™ ddPCR Mutation Assay Kit: EGFR WT for p.L858R, and EGFR p.L858R" was used.

2.3 Preparation of Reaction Unit

A PCR reaction of 20 μL prepared in the above table was added to a sample hole in a microdroplet occurrence card. Then 70 μL of microdroplet occurrence oil was added to an oil hole in the microdroplet occurrence card. Finally, the microdroplet occurrence card was sealed with a sealing strip.

The microdroplet occurrence card prepared above was then disposed into a droplet generator for the generation of microdroplets. About 2 minutes later, the preparation of the microdroplets was completed, and the microdroplet occurrence card was then dismounted, and a microdroplet suspension of about 40 μL was transferred from a top row of holes to a well of a 96-well PCR plate.

3. Amplification and Signal Reading

After sealing the 96-well PCR plates, they were placed in a PCR thermal cycler for PCR amplification. The PCR procedures is as follows: pre-denaturation at 95° C. for 10 minutes; denaturation at 94° C. for 30 seconds and annealing at 65° C. for 60 seconds, for five cycles; denaturation at 94° C. for 30 seconds and annealing at 55° C. for 60 seconds, for 40 cycles; inactivation at 98° C.; and terminating the PCR reaction at 10° C.

System 2 uses the following procedures: pre-denaturation at 95° C. for 10 minutes; denaturation at 94° C. for 30 seconds and annealing at 55° C. for 60 seconds, for a total of 40 cycles; inactivation at 98° C. for 10 minutes; and terminating the PCR reaction at 10° C.

At the end of the PCR amplification, the 96-well plates were placed in a microdroplet analyzer, and the FAM/HEX channel was selected for signal reading.

The QuantaSoft analysis software was used to analyze the intensity and number of fluorescent signals to thereby obtain the copy number and the concentration of the EGFR L858R mutant and the copy number and the concentration of the EGFR L858 wild type, based on which the mutant abundance was further calculated.

The scatter plot of the detection results of the fragmented DNA sample from the NCI-H1975 cell line (with a theoretical mutation abundance of 12%) using System 1 disclosed herein is shown in FIG. 6A, as compared with that shown in FIG. 6B using a comparative kit from Bio-Rad.

The detection results of the fragmented DNA sample from the NCI-H1975 cell line (with a theoretical mutation abundance of 12%) using system 1, system 2 and system 3, respectively, are summarized in Table. 8:

TABLE 8

|  | Concentration of Mutant Nucleic Acid (copies/μL) | | | | Concentration of Wild-type Nucleic Acid (copies/μL) | | | | Mutation Abundance (Mt/Mt + WT) % | | | |
|---|---|---|---|---|---|---|---|---|---|---|---|---|
| System 1 | 68.8 | 68.8 | 68.7 | 64.7 | 474 | 469 | 471 | 472 | 12.7 | 12.8 | 12.7 | 12.1 |
| System 2 | 62.1 | 63.2 | 66.0 | 61.7 | 423 | 451 | 444 | 444 | 12.8 | 12.3 | 12.9 | 12.2 |
| System 3 | 52.5 | 49.6 | 49.2 | 52.1 | 377 | 368 | 377 | 387 | 12.2 | 11.9 | 11.5 | 11.9 |
| Average of System 1 | 67.8 | | | | 471.5 | | | | 12.6 | | | |
| Average of System 2 | 63.3 | | | | 440.5 | | | | 12.6 | | | |

TABLE 8-continued

| | Concentration of Mutant Nucleic Acid (copies/μL) | Concentration of Wild-type Nucleic Acid (copies/μL) | Mutation Abundance (Mt/Mt + WT) % |
|---|---|---|---|
| Average of System 3 | 50.9 | 377.3 | 11.9 |

FIG. 7A, FIG. 7B, and FIG. 7C show the data analysis of the detection results using the EGFR L858R detection system 1, detection system 2 and detection system 3, respectively, over the fragmented DNA samples (having theoretical mutation abundance of 12%) obtained from the NCI-H1975 cell lines.

FIG. 7A shows the quantitative results of the concentrations of the wild-type target nucleic acid sequences. The paired t test performed between system 1, system 2 and system 3 shows that the P values were 0.004 (system 1 vs system 2) and 0.020 (system 2 vs system 3), respectively. Thus, there are statistically significant differences between these systems.

FIG. 7B shows the quantitative results of the concentrations of the mutant target nucleic acid sequences. The paired t-test performed between system 1, system 2 and system 3 shows that the P values were 0.006 (system 1 vs system 2) and 0.019 (system 2 vs system 3), respectively. Thus, there are statistically significant differences between these systems.

FIG. 7C shows the quantitative results of mutant abundance (i.e., mutant concentration/mutant concentration+ wild-type concentration). The paired t-test performed between system 1, system 2 and system 3 shows that the P values were 0.074 (system 1 vs system 2) and 0.886 (system 2 vs system 3), respectively. Thus, there are no statistically significant differences between these systems (ns).

As can be seen from FIGS. 7A, 7B and 7C, different amplificon lengths have significant differences in quantitative detection results. In the quantitative detection of fragmented DNA templates, shorter amplicon lengths can detect more target nucleic acid templates, resulting in generally a higher concentration and a higher copy number in the results, while still ensuring the consistency of mutation abundance.

The primers and probes and the detection method disclosed herein can thus effectively reduce the length of target nucleic acid fragments to be detected, and can in turn improve the detection rate of fragmented target nucleic acid templates. Therefore, the primers and kits disclosed herein can be used for detection of rare mutations, especially for the detection of tumor mutation target nucleic acids in peripheral blood samples or other body fluid samples, with a relatively better detection performance.

Example 5

In this example, DNA samples from the NCI-H1650 cell line were used to detect exon 19 mutation of human EGFR gene (e.g., the subtype EGFR p.E746_750del (c.2235_2249del15)), to test the performance of detecting deletions using the primer system disclosed herein.

1. Sample Preparation

DNA samples from the NCI-H1650 cell line containing the EGFR Exon 19 deletion were extracted using the QIAGENis QIAamp® DNA Mini Kit according to manufacturer's instructions, to thereby obtain a genomic DNA sample containing the EGFR Exon 19 deletion.

2. Reaction System 2.1 Primer and Probes

The primers and probes were synthesized from Sangon Biotech, Ltd.

The sequences for the primers and the probes are shown in Table 9 as follows:

TABLE 9

| Primers/Probes | | SEQ ID NO | Nucleotide sequence (from 5' end to 3' end) | Modification |
|---|---|---|---|---|
| EGFR Exon 19 Deletion Detection | mutant F1 | SEQ ID NO: 18 | CTTGCTCTCCGCTCATCTCCTAA CCGTTCCGCCTGTTCCTGGTCGC TATCCAAACATCTCCG | none |
| | wild-type F1 | SEQ ID NO: 19 | CCATTCGTCCTACTCTCATCATC TCTCGTCTCAGCCTCCATCCACG CTATCATGGAATTAAGAGAAGCA | none |
| | mutant F2 | SEQ ID NO: 20 | CTTGCTCTCCGCTCATC | none |
| | wild-type F2 | SEQ ID NO: 21 | CCATTCGTCCTACTCTCATC | none |
| | mutant probe P | SEQ ID NO: 22 | CTAACCGTTCCGCCTGTTCC | 5'FAM 3'BHQ1 |
| | wild-type probe P | SEQ ID NO: 23 | CTCTCGTCTCAGCCTCCATCC | 5'HEX 3'BHQ1 |
| | reverse primer R | SEQ ID NO: 24 | CAAAGCAGAAACTCACATCG | none |

The mutant F1 primer (as set forth in SEQ ID NO: 18) was designed to be directed to a common EGFR exon 19 deletion (EGFR p.E746_750del (c. 2235_2249del15)), with a mismatch base arranged at the 12$^{th}$ position from the 3' end thereof (shown by the underline). The wild-type F1 primer (as set forth in SEQ ID NO: 19) has a mismatch base arranged at the 17$^{th}$ position from the 3' end thereof (shown by the underline).

The 18/20 bases at the 5' end of each of the mutant F1 primer and the wild-type F1 primer are identical to those of their corresponding F2 primers (i.e., the mutant F2 primer and the wild-type F2 primer, set forth in SEQ ID NO: 20 and SEQ ID NO: 21, respectively). The sequence of a segment containing bases from the 20$^{th}$ base to the 39th base at the 5' end of the mutant F1 primer is identical as that of the corresponding mutant probe P (as set forth in SEQ ID NO: 22). The sequence of a segment containing bases from the 23$^{rd}$ to 43$^{rd}$ base at the 5' end of the wild-type F1 primer is identical as that of the corresponding wild-type probe P (SEQ ID NO: 23).

2.2 Reaction System:

The primer system disclosed herein is substantially same as that in Example 1 as described above.

A comparative experiment running in parallel was set up, where the "PrimePCR ddPCR Mutation Assay Kit: EGFR WT for p.E746_A750del, and EGFR p.E746_A750del" (#1863105) from Bio-Rad was used as a comparative kit, and the reaction was set up according to the manufacturer's instructions.

3. Preparation of Reaction Unit

A PCR reaction of 20 µL prepared in the above table was added to a sample hole in a microdroplet occurrence card. Then 70 µL of microdroplet occurrence oil was added to an oil hole in the microdroplet occurrence card. Finally, the microdroplet occurrence card was sealed with a sealing strip.

The microdroplet occurrence card prepared above was then disposed into a droplet generator for the generation of microdroplets. About 2 minutes later, the preparation of the microdroplets was completed, and the microdroplet occurrence card was then dismounted, and a microdroplet suspension of about 40 µL was transferred from a top row of holes to a well of a 96-well PCR plate.

4. Amplification and Signal Reading

After sealing the 96-well PCR plates, they were placed in a PCR thermal cycler for PCR amplification. The PCR procedures is as follows: pre-denaturation at 95° C. for 10 minutes; denaturation at 94° C. for 30 seconds and annealing at 65° C. for 60 seconds, for five cycles; denaturation at 94° C. for 30 seconds and annealing at 55° C. for 60 seconds, for 40 cycles; inactivation at 98° C.; and terminating the PCR reaction at 10° C.

Bio-Rad's comparative kit uses the following procedures: pre-denaturation at 95° C. for 10 minutes; denaturation at 94° C. for 30 seconds and annealing at 55° C. for 60 seconds, for a total of 40 cycles; inactivation at 98° C. for 10 minutes; and terminating the PCR reaction at 10° C.

At the end of the PCR amplification, the 96-well plates were placed in a microdroplet analyzer, and the FAM/HEX channel was selected for signal reading.

5. Statistics and Analysis

The QuantaSoft analysis software was used to analyze the intensity and number of fluorescent signals to thereby obtain the copy number and the concentration of the EGFR L858R mutant and the copy number and the concentration of the EGFR L858 wild type, based on which the mutant abundance was further calculated.

FIG. 8A shows a scatter plot for the detection results of the EGFR exon 19 deletion using the control reagent (i.e., the PrimePCR ddPCR Mutation Assay Kit: EGFR WT for p.E746_A750del, and EGFR p.E746_A750del (#1863105) from Bio-Rad), and FIG. 8B shows a scatter plot for the detection results of the same mutation using the primers and probes provided in this present disclosure. As shown in the two plots, the threshold division for the detection kit and method provided in this present disclosure and for the comparative kit (control) was both accurate, and the detection performance was also similar.

The same DNA sample from the NCI-H1650 cell line was tested and quantified using the kit provided in this disclosure and using the Bio-Rad comparative kit. The average mutation abundance obtained for the two quantitative kits were 68.82% and 68.20%, respectively. No significant difference (P=0.287) was observed.

As illustrated by the grey circles in both FIGS. 8A and 8B, compared with the detection results using the comparative kit, the double positive fluorescence signals (i.e., within the upper right quadrant) in the detection results using the kit provided herein was easier to distinguish from the single positive mutant signals (i.e., within the upper left quadrant). In addition, for the detection results using the kit disclosed herein, the cross-reaction was smaller where both the wild-type and mutant types were simultaneously detected, and the interference of the fluorescence signal intensity of the double positive microdroplets was also smaller, compared with the detection results using the comparative kit. Thus, the kit and method disclosed herein is more advantageous to detecting target nucleic acids containing rare mutations.

Example 6

In the early stage of research and development, various designs and various experimental schemes have been attempted. In addition to the above examples, which mainly present optimized or preferred kits and methods, there can be other examples, and the example will be provided in the following as an illustrating example.

1. Sample Preparation

Fragmented DNA samples from the Colo 205 cell line, which contain the BRAF V600E mutation with a theoretical mutation abundance of 65.8%, were quantified by digital PCR and used to simulate clinical circulating tumor DNA (ctDNA) samples.

Genomic DNA from healthy people was also prepared. After the second-generation sequencing confirmed that there was no BRAF V600E mutation, the genomic DNA also underwent enzymatic fragmentation to thereby obtain a fragmented wild-type DNA sample to simulate a clinical cell-free DNA sample.

2. Reaction System:

2.1 Primers and Probes

The method of the primers and probes disclosed herein is shown in FIG. 9. Two different forward primers F were used to amplify the mutant target nucleic acid sequences and the wild-type target nucleic acid sequences. Because the mutation sites or the SNPs (single-nucleotide polymorphisms) at the 3' end of the target nucleic acid sequence are not sufficient to block the amplification reaction. Therefore, a segment having 1-15 mismatched bases was added near the 3' end to enhance the blocking effect, so as to improve the specificity of primers.

A segment that does not sequentially match the template was added at the 5' end of the forward primer F, which has a sequence that is configured to be completely complementary to the sequence of the probe P. Therefore, two different probes P were configured to pair with the 5' end of the corresponding mutant forward primer F and the wild-type forward primer F, respectively. A reverse primer R was designed corresponding to a region around 50-200 bp downstream of the forward primer F. In the process of amplification and extension of the reverse primer R, it is theoretically assumed that the probe P, which was complementary to the 5' end of the forward primer F, could be hydrolyzed to thereby release fluorescent signals.

The primers and the probes used in this specific example are summarized in Table 10.

TABLE 10

| Primers/Probes | | SEQ ID NO | Nucleotide sequence (from 3' end to 5' end) | Modification |
|---|---|---|---|---|
| BRAF V600E mutation Detection (As control) | mutant F | SEQ ID NO: 25 | AGCCACTGCTCGCACAGATTTTGGTCTAGCTACTGA | none |
| | wild-type F | SEQ ID NO: 26 | CCCGTCTCGCAGGAACGATTTTGGTCTAGCTACGGT | none |
| | mutant probe P | SEQ ID NO: 27 | TGCGAGCAGTGGC | 5'FAM 3'MGB |
| | wild-type probe P | SEQ ID NO: 28 | TCCTGCGAGACGG | 5'HEX 3'MGB |
| | revere primer P | SEQ ID NO: 29 | CCTCAATTCTTACCATCC | none |

2.2 Reaction System

The PCR reaction system disclosed in this example is substantially same as that in Example 1 as described above.

2.3 Preparation of Reaction Unit

A PCR reaction of 20 μL prepared in the above table was added to a sample hole in a microdroplet occurrence card. Then 70 μL of microdroplet occurrence oil was added to an oil hole in the microdroplet occurrence card. Finally, the microdroplet occurrence card was sealed with a sealing strip.

The microdroplet occurrence card prepared above was then disposed into a droplet generator for the generation of microdroplets. About 2 minutes later, the preparation of the microdroplets was completed, and the microdroplet occurrence card was then dismounted, and a microdroplet suspension of about 40 μL was transferred from a top row of holes to a well of a 96-well PCR plate.

3. Amplification and Signal Reading

After sealing the 96-well PCR plates, they were placed in a PCR thermal cycler for PCR amplification. The PCR procedures is as follows: pre-denaturation at 95° C. for 10 minutes; denaturation at 94° C. for 30 seconds and annealing at 65° C. for 60 seconds, for five cycles; denaturation at 94° C. for 30 seconds and annealing at 55° C. for 60 seconds, for 40 cycles; inactivation at 98° C.; and terminating the PCR reaction at 10° C.

At the end of the PCR amplification, the 96-well plates were placed in a microdroplet analyzer, and the FAM/HEX channel was selected for signal reading.

4. Fluorescent Quantitative PCR

The design was tested by means of a fluorescence quantitative PCR. The reaction system was prepared as follows:

TABLE 11

| Reagents | | Concentration in final reaction |
|---|---|---|
| BRAF V600E mutation Detection | mutant F | 500 nM |
| | wild-type F | 500 nM |
| | mutant probe P | 250 nM |
| | wild-type probe P | 250 nM |
| | revere primer P | 500 nM |
| | DNA sample | 0.5 ng/μL |
| | ddH$_2$O | Til 20 μL |
| | mutant F | 500 nM |

The Applied Biosystems 7500 real-time fluorescence quantitative PCR system was used for the fluorescence quantitative PCR. The PCR procedure used was: pre-denaturation at 95° C. for 10 minutes; denaturation at 94° C. for 30 seconds and annealing at 55° C. for 60 seconds, a total of 40 cycles; inactivation at 98° C. for 10 minutes; and termination at 10° C.

After the end of the PCR procedure, the results of the fluorescence quantitative PCR were analyzed by the ABI-7500 Software v2.3, to thereby obtain the amplification curves of the mutant target nucleic acids and the wild type target nucleic acids.

The QuantaSoft analysis software was used to analyze the intensity and number of fluorescent signals to thereby obtain the copy number and the concentration of the BRAF V600E mutant and the copy number and the concentration of the BRAF V600 wild type, based on which the mutant abundance was further calculated.

FIG. 10A and FIG. 10B show the detection results of fragmented DNA samples from the Colo 205 cell lines with theoretical mutation abundance of 65.8%, where the results of fluorescence quantitative PCR were shown in FIG. 10A and the results of digital PCR were shown in FIG. 10B.

Both methods reflect a same issue, that is, no positive signals can be detected. It was speculated that the issue is caused by the fact that the probe pairs directly with the primer, which in turn causes that the fluorescence signal can be released by the probe even in the absence of the target nucleic acid template. As such, there are no negative background signals in all detection results, that is, the positive and negative samples cannot be distinguished.

By introducing an improvement in the scheme so that the probe could not be directly paired with any primers, the situation that the probe emits signals without the target nucleic acid template can thus be avoided. This improved method substantially forms the preferred examples of the kit and the method described above.

Although specific examples have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A component configured to perform digital PCR, comprising a primer as a first forward primer to detect a target nucleic acid in a sample, the primer comprising:
   - a target sequence binding portion; and
   - a detection portion located upstream to the target sequence binding portion, wherein
   said detection portion comprises:
   - a second forward primer binding portion having a sequence substantially complementary to a second forward primer, and
   - a probe binding portion downstream to the second forward primer binding portion having a sequence substantially complementary to a probe; and
   said target sequence binding portion comprises:
   - a mismatch portion having a sequence not complementary to the target nucleic acid, and
   - an amplification determinant portion different from, and downstream, to the mismatch portion, the amplification determinant portion having a sequence complementary to a gene allele or a variant thereof encoded by the target nucleic acid;
   wherein there are no other bases downstream of the amplification determinant portion.

2. The component according to claim 1,
   comprising a primer set including:
   the first forward primer;
   the second forward primer;
   the probe having a sequence complementary to a reporter binding portion; and
   a reverse primer having a sequence complementary to a complementary region on the target nucleic acid.

3. The component of claim 2, wherein the complementary region on the target nucleic acid is about 50-200 bp downstream of a complementary region between the first forward primer and the target sequence.

4. The component of claim 2, wherein the first forward primer and the second forward primer have different Tm values.

5. The component claim 2, wherein the mismatch portion has a length of 1-15 bases.

6. The component of claim 2, wherein a distance between the amplification determinant portion and the mismatch portion is about 0-20 bases.

7. The component of claim 2, wherein the upstream detection portion is configured not to sequentially match or complement with the target sequence, or to hybridize with the target nucleic acid under a stringent condition.

8. The component of claim 2, wherein variation of the allele sequence is a point mutation.

9. A method for detecting a sequence variation of a target nucleic acid in a sample using digital PCR with the component of claim 2, wherein said sample is diluted to a limit and distributed randomly to 770-10,000,000 fractions, each fraction containing the primer set for simultaneous amplification across all fractions in a uniform thermal cycle, said method comprising:
   maintaining a reaction condition to allow the primer set to form pre-amplification complexes;
   initiating amplification reactions;
   detecting signals emitted from the probes in each fraction; and
   determining a quantitation for the target nucleic acid in the sample based on the signals detected.

10. The method of claim 9, wherein the complementary region between the reverse primer and the target nucleic acid is around 50-200 bp downstream of a complementary region between the first forward primer and the target sequence.

11. The method of claim 9, wherein a length of the mismatch portion is about 1-15 bases.

12. The method of claim 9, wherein a distance between the amplification determinant site portion and the mismatch portion is about 0-20 bases.

13. The method of claim 9, wherein the upstream detection portion of the first forward primer is configured not to sequentially match or complement with the target sequence, or to hybridize with the target nucleic acid under a stringent condition.

14. The method of claim 9, wherein said maintaining is performed at a different temperature from the said initiating.

15. The method of claim 9, wherein the first forward primer and the second forward primer are configured to have a different Tm value.

16. The method of claim 9, wherein said maintaining further comprising maintaining reaction conditions to allow 3-10 thermal cycles for the pre-amplification complexes to form.

17. The method of claim 9, wherein a variation of the sequence variation of the allele is a point mutation.

18. The method of claim 9, wherein the primer set includes multiple species of first forward primers and multiple species of probes.

19. A composition, comprising:
   a molecular complex formed by a target nucleic acid encoding a target sequence, a first forward primer, a second forward primer, and a probe in complex with each other, wherein:
   said first forward primer comprising:
   a target sequence binding portion; and
   a detection portion upstream of the target sequence binding portion, and wherein:
   said detection portion comprises a second forward primer binding portion encoding a sequence complementary to the second forward primer located upstream to a reporter binding portion encoding a sequence complementary to the probe; and
   said target sequence binding portion comprises:
   a mismatch portion having a sequence not complementary to the target nucleic acid, and
   an amplification determinant portion, different from, and downstream to, the mismatch portion, the amplification determinant portion having a sequence complementary to a gene allele or a variant thereof encoded by the target nucleic acid;
   wherein there are no other bases downstream of the amplification determinant portion.

20. A kit comprising the component of claim 2, and configured to perform digital PCR to detect at least one allele of a sequence variation of a target nucleic acid, the kit comprising:
   at least one primer set,
   wherein said target sequence binding portion encodes a sequence complementary to the sequence of the allele or a variation thereof.

* * * * *

SEQUENCE LISTING

<160> NUMBER OF SEQ ID NOS: 29

<210> SEQ ID NO 1
<211> LENGTH: 62
<212> TYPE: DNA
<213> ORGANISM: Artificial Sequence
<220> FEATURE:
<223> OTHER INFORMATION: BRAF V600E mutant primer F1 (1-bp mismatch)

<400> SEQUENCE: 1
accgacagtg gtacgcaacg attcctatgc tcgctgtcgg gtgattttgg tctagctact    60
ga    62

<210> SEQ ID NO 2
<211> LENGTH: 61
<212> TYPE: DNA
<213> ORGANISM: Artificial Sequence
<220> FEATURE:
<223> OTHER INFORMATION: BRAF V600 wildtype primer F1 (1-bp mismatch)

<400> SEQUENCE: 2
gcgtcacgtc ctgaagcagt cgtttcgcag atcgctcggg tgattttggt ctagctacgg    60
t    61

<210> SEQ ID NO 3
<211> LENGTH: 16
<212> TYPE: DNA
<213> ORGANISM: Artificial Sequence
<220> FEATURE:
<223> OTHER INFORMATION: BRAF V600E mutant primer F2

<400> SEQUENCE: 3
accgacagtg gtacgc    16

<210> SEQ ID NO 4
<211> LENGTH: 16
<212> TYPE: DNA
<213> ORGANISM: Artificial Sequence
<220> FEATURE:
<223> OTHER INFORMATION: BRAF V600 wildtype primer F2

<400> SEQUENCE: 4
gcgtcacgtc ctgaag    16

<210> SEQ ID NO 5
<211> LENGTH: 20
<212> TYPE: DNA
<213> ORGANISM: Artificial Sequence
<220> FEATURE:
<223> OTHER INFORMATION: probe for BRAF V600E mutant

<400> SEQUENCE: 5
acgattccta tgctcgctgt    20

<210> SEQ ID NO 6
<211> LENGTH: 19
<212> TYPE: DNA
<213> ORGANISM: Artificial Sequence
<220> FEATURE:
<223> OTHER INFORMATION: probe for BRAF V600 wildtype

<400> SEQUENCE: 6
agtcgtttcg cagatcgct    19

```
<210> SEQ ID NO 7
<211> LENGTH: 22
<212> TYPE: DNA
<213> ORGANISM: Artificial Sequence
<220> FEATURE:
<223> OTHER INFORMATION: reverse primer for BRAF V600 detection

<400> SEQUENCE: 7
cctcaattct taccatccac aa                                           22

<210> SEQ ID NO 8
<211> LENGTH: 78
<212> TYPE: DNA
<213> ORGANISM: Artificial Sequence
<220> FEATURE:
<223> OTHER INFORMATION: BRAF V600E mutant primer F1 (14-bp mismatch)

<400> SEQUENCE: 8
accgacagtg gtacgcaacg attcctatgc tcgctgtcgc ctcacagtaa aaataggaat   60
catcaacatc tctacaga                                                78

<210> SEQ ID NO 9
<211> LENGTH: 77
<212> TYPE: DNA
<213> ORGANISM: Artificial Sequence
<220> FEATURE:
<223> OTHER INFORMATION: BRAF V600 wildtype primer F1 (14-bp mismatch)

<400> SEQUENCE: 9
gcgtcacgtc ctgaagcagt cgtttcgcag atcgctcgcc tcacagtaaa aataggtatc   60
cataatactc ctacagt                                                 77

<210> SEQ ID NO 10
<211> LENGTH: 69
<212> TYPE: DNA
<213> ORGANISM: Artificial Sequence
<220> FEATURE:
<223> OTHER INFORMATION: EGFR L858R mutant primer F1

<400> SEQUENCE: 10
taccgacagt ggtacgcaac gattcctatg ctcgctgtcg gtcaagatca cagattttgg   60
actagtccg                                                          69

<210> SEQ ID NO 11
<211> LENGTH: 71
<212> TYPE: DNA
<213> ORGANISM: Artificial Sequence
<220> FEATURE:
<223> OTHER INFORMATION: EGFR L858 wildtype primer F1

<400> SEQUENCE: 11
cacagtcgtg cctccatcat cgcacctacc gcagactcgc atgtcaagat cacagattac   60
atgtctgggc t                                                       71

<210> SEQ ID NO 12
<211> LENGTH: 16
<212> TYPE: DNA
<213> ORGANISM: Artificial Sequence
<220> FEATURE:
<223> OTHER INFORMATION: EGFR L858R mutant primer F2

<400> SEQUENCE: 12
accgacagtg gtacgc                                                  16
```

<210> SEQ ID NO 13
<211> LENGTH: 19
<212> TYPE: DNA
<213> ORGANISM: Artificial Sequence
<220> FEATURE:
<223> OTHER INFORMATION: EGFR L858 wildtype primer F2

<400> SEQUENCE: 13
cacagtcgtg cctccatca                                              19

<210> SEQ ID NO 14
<211> LENGTH: 20
<212> TYPE: DNA
<213> ORGANISM: Artificial Sequence
<220> FEATURE:
<223> OTHER INFORMATION: probe for EGFR L858R mutant

<400> SEQUENCE: 14
acgattccta tgctcgctgt                                             20

<210> SEQ ID NO 15
<211> LENGTH: 19
<212> TYPE: DNA
<213> ORGANISM: Artificial Sequence
<220> FEATURE:
<223> OTHER INFORMATION: probe for EGFR L858 wildtype

<400> SEQUENCE: 15
cgcacctacc gcagactcg                                              19

<210> SEQ ID NO 16
<211> LENGTH: 20
<212> TYPE: DNA
<213> ORGANISM: Artificial Sequence
<220> FEATURE:
<223> OTHER INFORMATION: reverse primer for EGFR L858 detection
      (reaction system 1)

<400> SEQUENCE: 16
atggtattct ttctcttccg                                             20

<210> SEQ ID NO 17
<211> LENGTH: 20
<212> TYPE: DNA
<213> ORGANISM: Artificial Sequence
<220> FEATURE:
<223> OTHER INFORMATION: reverse primer for EGFR L858 detection
      (reaction system 3)

<400> SEQUENCE: 17
ctccttactt tgcctccttc                                             20

<210> SEQ ID NO 18
<211> LENGTH: 62
<212> TYPE: DNA
<213> ORGANISM: Artificial Sequence
<220> FEATURE:
<223> OTHER INFORMATION: EGFR 19-del mutant F1

<400> SEQUENCE: 18
cttgctctcc gctcatctcc taaccgttcc gctgttcct ggtcgctatc caaacatctc   60
cg                                                                62

<210> SEQ ID NO 19
<211> LENGTH: 69

<212> TYPE: DNA
<213> ORGANISM: Artificial Sequence
<220> FEATURE:
<223> OTHER INFORMATION: EGFR 19-del wildtypeF1

<400> SEQUENCE: 19
ccattcgtcc tactctcatc atctctcgtc tcagcctcca tccacgctat catggaatta        60
agagaagca                                                                69

<210> SEQ ID NO 20
<211> LENGTH: 18
<212> TYPE: DNA
<213> ORGANISM: Artificial Sequence
<220> FEATURE:
<223> OTHER INFORMATION: EGFR 19-del mutant F2

<400> SEQUENCE: 20
cttgctctcc gctcatct                                                      18

<210> SEQ ID NO 21
<211> LENGTH: 20
<212> TYPE: DNA
<213> ORGANISM: Artificial Sequence
<220> FEATURE:
<223> OTHER INFORMATION: EGFR 19-de wildtypeF2

<400> SEQUENCE: 21
ccattcgtcc tactctcatc                                                    20

<210> SEQ ID NO 22
<211> LENGTH: 20
<212> TYPE: DNA
<213> ORGANISM: Artificial Sequence
<220> FEATURE:
<223> OTHER INFORMATION: EGFR 19-del mutant probe

<400> SEQUENCE: 22
ctaaccgttc cgcctgttcc                                                    20

<210> SEQ ID NO 23
<211> LENGTH: 21
<212> TYPE: DNA
<213> ORGANISM: Artificial Sequence
<220> FEATURE:
<223> OTHER INFORMATION: EGFR 19-de wildtype probe

<400> SEQUENCE: 23
ctctcgtctc agcctccatc c                                                  21

<210> SEQ ID NO 24
<211> LENGTH: 20
<212> TYPE: DNA
<213> ORGANISM: Artificial Sequence
<220> FEATURE:
<223> OTHER INFORMATION: reverse primer for EGFR 19-del

<400> SEQUENCE: 24
caaagcagaa actcacatcg                                                    20

<210> SEQ ID NO 25
<211> LENGTH: 36
<212> TYPE: DNA
<213> ORGANISM: Artificial Sequence
<220> FEATURE:
<223> OTHER INFORMATION: BRAF V600E mutant primer F(comparison solution)

```
<400> SEQUENCE: 25
agccactgct cgcacagatt ttggtctagc tactga                              36

<210> SEQ ID NO 26
<211> LENGTH: 36
<212> TYPE: DNA
<213> ORGANISM: Artificial Sequence
<220> FEATURE:
<223> OTHER INFORMATION: BRAF V600 wildtype primer F (comparison
      solution)

<400> SEQUENCE: 26
cccgtctcgc aggaacgatt ttggtctagc tacggt                              36

<210> SEQ ID NO 27
<211> LENGTH: 13
<212> TYPE: DNA
<213> ORGANISM: Artificial Sequence
<220> FEATURE:
<223> OTHER INFORMATION: probe for BRAF V600E mutant (comparison
      solution)

<400> SEQUENCE: 27
tgcgagcagt ggc                                                       13

<210> SEQ ID NO 28
<211> LENGTH: 13
<212> TYPE: DNA
<213> ORGANISM: Artificial Sequence
<220> FEATURE:
<223> OTHER INFORMATION: probe for BRAF V600 wildtype (comparison
      solution)

<400> SEQUENCE: 28
tcctgcgaga cgg                                                       13

<210> SEQ ID NO 29
<211> LENGTH: 18
<212> TYPE: DNA
<213> ORGANISM: Artificial Sequence
<220> FEATURE:
<223> OTHER INFORMATION: reverse primer for BRAF V600 (comparison
      solution)

<400> SEQUENCE: 29
cctcaattct taccatcc                                                  18
```